(12) United States Patent
Boudreaux et al.

(10) Patent No.: US 9,510,906 B2
(45) Date of Patent: Dec. 6, 2016

(54) TISSUE CLAMPING FEATURES OF SURGICAL INSTRUMENT END EFFECTOR

(71) Applicant: Ethicon Endo-Surgery, Inc., Cincinnati, OH (US)

(72) Inventors: Chad P. Boudreaux, Cincinnati, OH (US); Geoffrey S. Strobl, Williamsburg, OH (US); Jonathan T. Batross, Mason, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 520 days.

(21) Appl. No.: 13/832,197

(22) Filed: Mar. 15, 2013

(65) Prior Publication Data
US 2014/0276735 A1    Sep. 18, 2014

(51) Int. Cl.
| | | |
|---|---|---|
| *A61B 18/18* | (2006.01) | |
| *A61B 18/08* | (2006.01) | |
| *A61B 17/29* | (2006.01) | |
| *A61B 18/14* | (2006.01) | |

(52) U.S. Cl.
CPC ............... *A61B 18/18* (2013.01); *A61B 17/29* (2013.01); *A61B 18/085* (2013.01); *A61B 18/148* (2013.01); *A61B 18/1445* (2013.01); *A61B 2017/2934* (2013.01); *A61B 2017/2937* (2013.01); *A61B 2017/2939* (2013.01); *A61B 2017/2944* (2013.01); *A61B 2018/1455* (2013.01)

(58) Field of Classification Search
CPC ................. A61B 2017/2923; A61B 17/07207; A61B 17/295; A61B 18/1445; A61B 2017/00398; A61B 2017/07214; A61B 2017/07285; A61B 2017/2922; A61B 2018/00345; A61B 2018/00404; A61B 2018/00601; A61B 2018/0061
See application file for complete search history.

(56) References Cited

U.S. PATENT DOCUMENTS

| | | |
|---|---|---|
| 4,805,823 A | 2/1989 | Rothfuss |
| 5,307,976 A | 5/1994 | Olson et al. |
| 5,415,334 A | 5/1995 | Williamson, IV et al. |
| 5,465,895 A | 11/1995 | Knodel et al. |
| 5,597,107 A | 1/1997 | Knodel et al. |
| 5,632,432 A | 5/1997 | Schulze et al. |

(Continued)

OTHER PUBLICATIONS

U.S. Appl. No. 61/410,603, filed Nov. 5, 2010.
International Search Report and Written Opinion dated Sep. 15, 2014 for Application No. PCT/US2014/016882.

*Primary Examiner* — Rex R Holmes
(74) *Attorney, Agent, or Firm* — Frost Brown Todd LLC

(57) ABSTRACT

An apparatus comprises a body, a shaft assembly, and an end effector. The shaft assembly extends distally from the body. The end effector is in communication with the shaft assembly. The end effector comprises a first jaw and a second jaw. The second jaw comprises a proximal portion and a distal portion. The second jaw is moveable relative to the first jaw between a first position, a second position, and a third position. The second jaw in the first position is open relative to the first jaw. The second jaw in the second position is positioned such that the distal portion is closer to the first jaw than the proximal portion. The second jaw in the third position is parallel the first jaw.

17 Claims, 25 Drawing Sheets

(56) References Cited

U.S. PATENT DOCUMENTS

| | | |
|---|---|---|
| 5,673,840 A | 10/1997 | Schulze et al. |
| 5,704,534 A | 1/1998 | Huitema et al. |
| 5,814,055 A | 9/1998 | Knodel et al. |
| 6,053,933 A | 4/2000 | Balazs et al. |
| 6,500,176 B1 | 12/2002 | Truckai et al. |
| 6,783,524 B2 | 8/2004 | Anderson et al. |
| 6,818,007 B1 | 11/2004 | Dampney et al. |
| 6,978,921 B2 | 12/2005 | Shelton, IV et al. |
| 7,000,818 B2 | 2/2006 | Shelton, IV et al. |
| 7,112,201 B2 | 9/2006 | Truckai et al. |
| 7,125,409 B2 | 10/2006 | Truckai et al. |
| 7,143,923 B2 | 12/2006 | Shelton, IV et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,303,108 B2 | 12/2007 | Shelton, IV et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,367,485 B2 | 5/2008 | Shelton, IV et al. |
| 7,380,695 B2 * | 6/2008 | Doll et al. ............... 227/175.1 |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,434,715 B2 | 10/2008 | Shelton, IV et al. |
| 7,721,930 B2 | 5/2010 | McKenna et al. |
| 8,408,439 B2 | 4/2013 | Huang et al. |
| 8,409,200 B2 | 4/2013 | Holcomb et al. |
| 8,453,914 B2 | 6/2013 | Laurent et al. |
| 8,461,744 B2 | 6/2013 | Wiener et al. |
| 8,616,427 B2 | 12/2013 | Viola |
| 2004/0094597 A1 * | 5/2004 | Whitman ......... A61B 17/07207 227/180.1 |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0078800 A1 * | 4/2008 | Hess ................ A61B 17/0644 227/175.1 |
| 2008/0200940 A1 | 8/2008 | Eichmann et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 * | 4/2011 | Boudreaux et al. ............ 606/41 |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0080477 A1 * | 4/2012 | Leimbach ......... A61B 17/07207 227/175.2 |
| 2012/0083783 A1 | 4/2012 | Davison et al. |
| 2012/0116379 A1 | 5/2012 | Yates et al. |
| 2013/0023868 A1 | 1/2013 | Worrell et al. |
| 2013/0030428 A1 | 1/2013 | Worrell et al. |

* cited by examiner

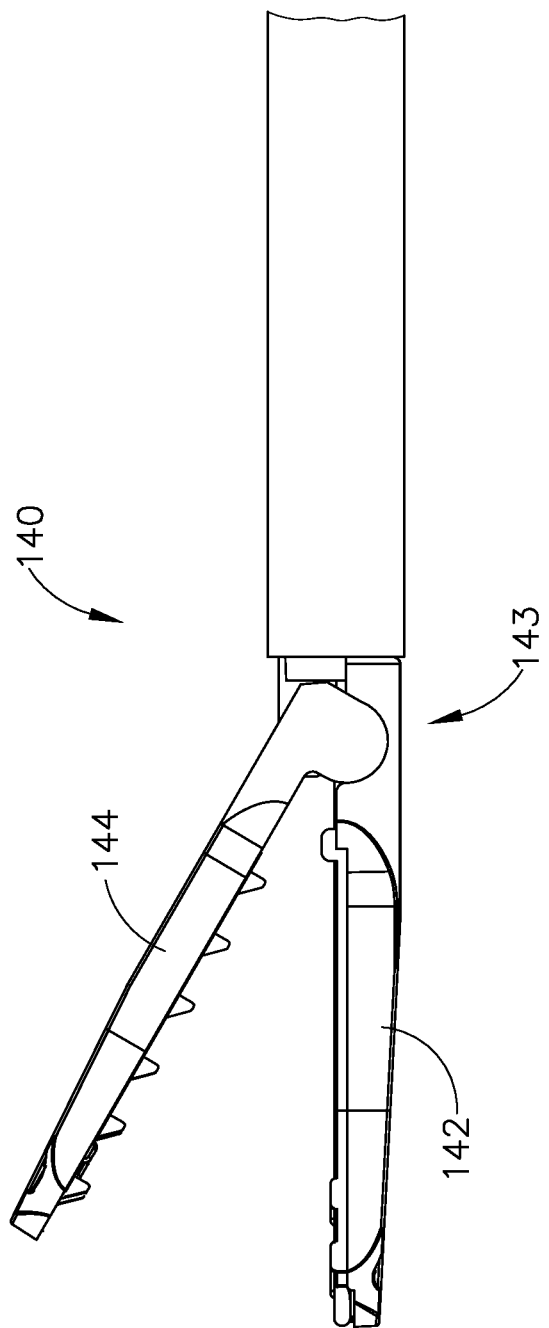

TISSUE CLAMPING FEATURES OF SURGICAL INSTRUMENT END EFFECTOR

BACKGROUND

A variety of surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. Pub. No. 2012/0083783, entitled "Surgical Instrument with Jaw Member," published Apr. 5, 2012, now U.S. Pat. No. 8,888,809, issued Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, the disclosure of which is incorporated by reference herein.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts a side, elevation view of an exemplary alternative end effector that may be incorporated into the electrosurgical medical instrument of FIG. 1;

Figure 1:
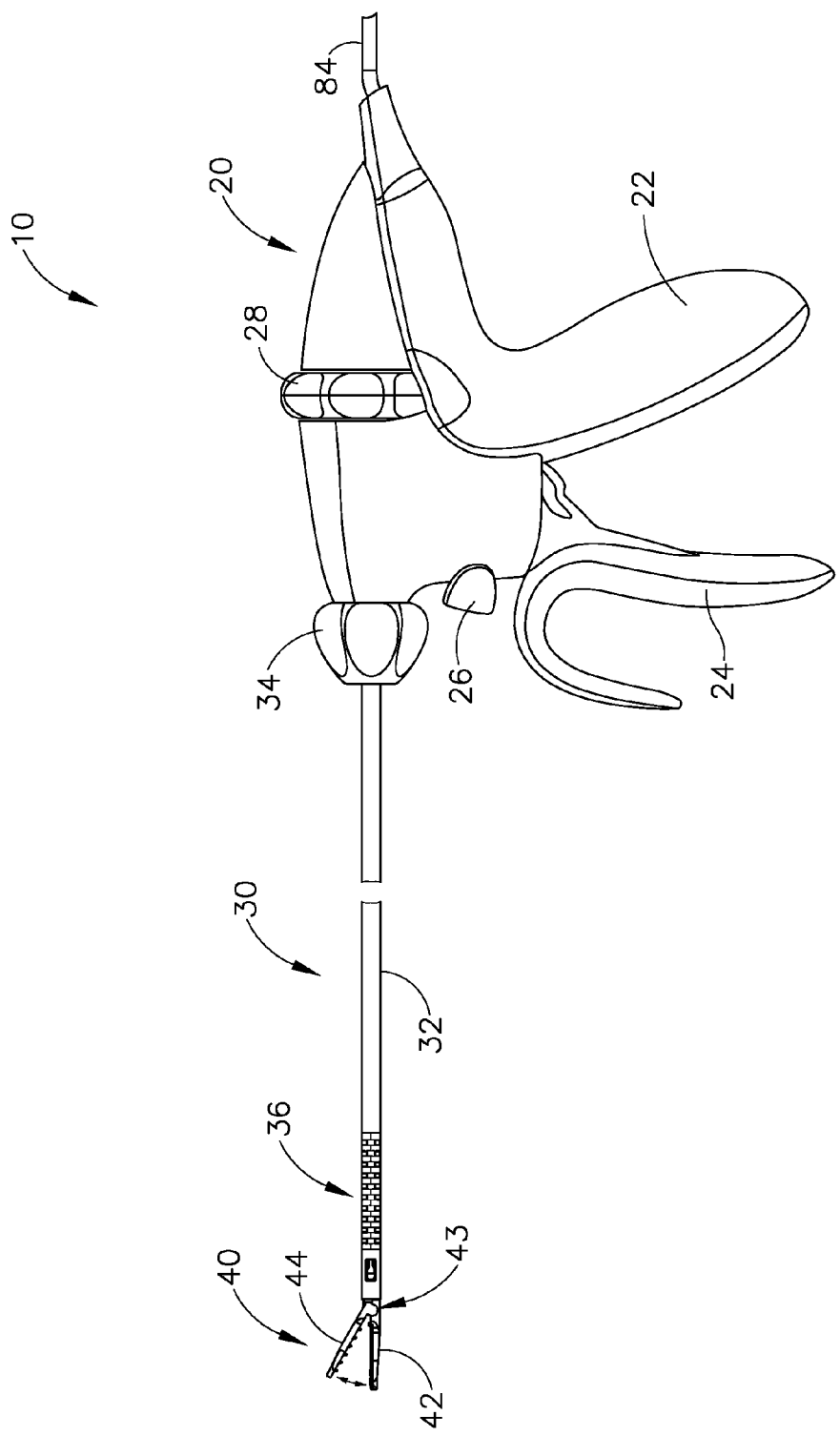
FIG. 1 depicts a side elevational view of an exemplary electrosurgical medical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974; U.S. Pub. No. 2012/0083783, now U.S. Pat. No. 8,888,809; U.S. Pub. No. 2012/0116379, now U.S. Pat. No. 9,161,803; U.S. Pub. No. 2012/0078243; U.S. Pub. No. 2012/0078247, now U.S. Pat. No. 9,402,682; U.S. Pub. No. 2013/0030428, now U.S. Pat. No. 9,089,327; and/or U.S. Pub. No. 2013/0023868. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes a rigid outer sheath (32) and an articulation section (36). Articulation section (36) is operable to selectively laterally deflect end effector (40) at various angles relative to the longitudinal axis defined by sheath (32). In some versions, articulation section (36) and/or some other portion of outer sheath (32) includes a flexible outer sheath (e.g., a heat shrink tube, etc.) disposed about its exterior. Articulation section (36) of shaft (30) may take a variety of forms. By way of example only, articulation section (36) may be configured in accordance with one or more teachings of U.S. Pub. No. 2012/0078247, now U.S. Pat. No. 9,402,682, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating articulation section (36) or any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating articulation section (36) or any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively laterally deflect end effector (40) at various angles relative to the longitudinal axis defined by shaft (30). While articulation control (28) is in the form of a rotary dial in the present example, it should be understood that articulation control (28) may take numerous other forms. By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. Pub. No. 2013/0023868, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

End effector (40) of the present example comprises a first jaw (42) and a second jaw (44). In the present example, first jaw (42) is substantially fixed relative to shaft (30); while second jaw (44) pivots relative to shaft (30), toward and away from first jaw (42). Use of the term "pivot" should not be read as necessarily requiring pivotal movement about a fixed axis. In some versions, second jaw (44) pivots about an axis that is defined by a pin (or similar feature) that slides along an elongate slot or channel as second jaw (44) moves toward first jaw (42). In such versions, the pivot axis translates along the path defined by the slot or channel while second jaw (44) simultaneously pivots about that axis. It should be understood that such sliding/translating pivotal movement is encompassed within terms such as "pivot," "pivots," "pivotal," "pivotable," "pivoting," and the like. Of course, some versions may provide pivotal movement of second jaw (44) about an axis that remains fixed and does not translate within a slot or channel, etc.

In some versions, actuators such as rods or cables, etc., may extend through sheath (32) and be joined with second jaw (44) at a pivotal coupling (43), such that longitudinal movement of the actuator rods/cables/etc. through shaft (30) provides pivoting of second jaw (44) relative to shaft (30) and relative to first jaw (42). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
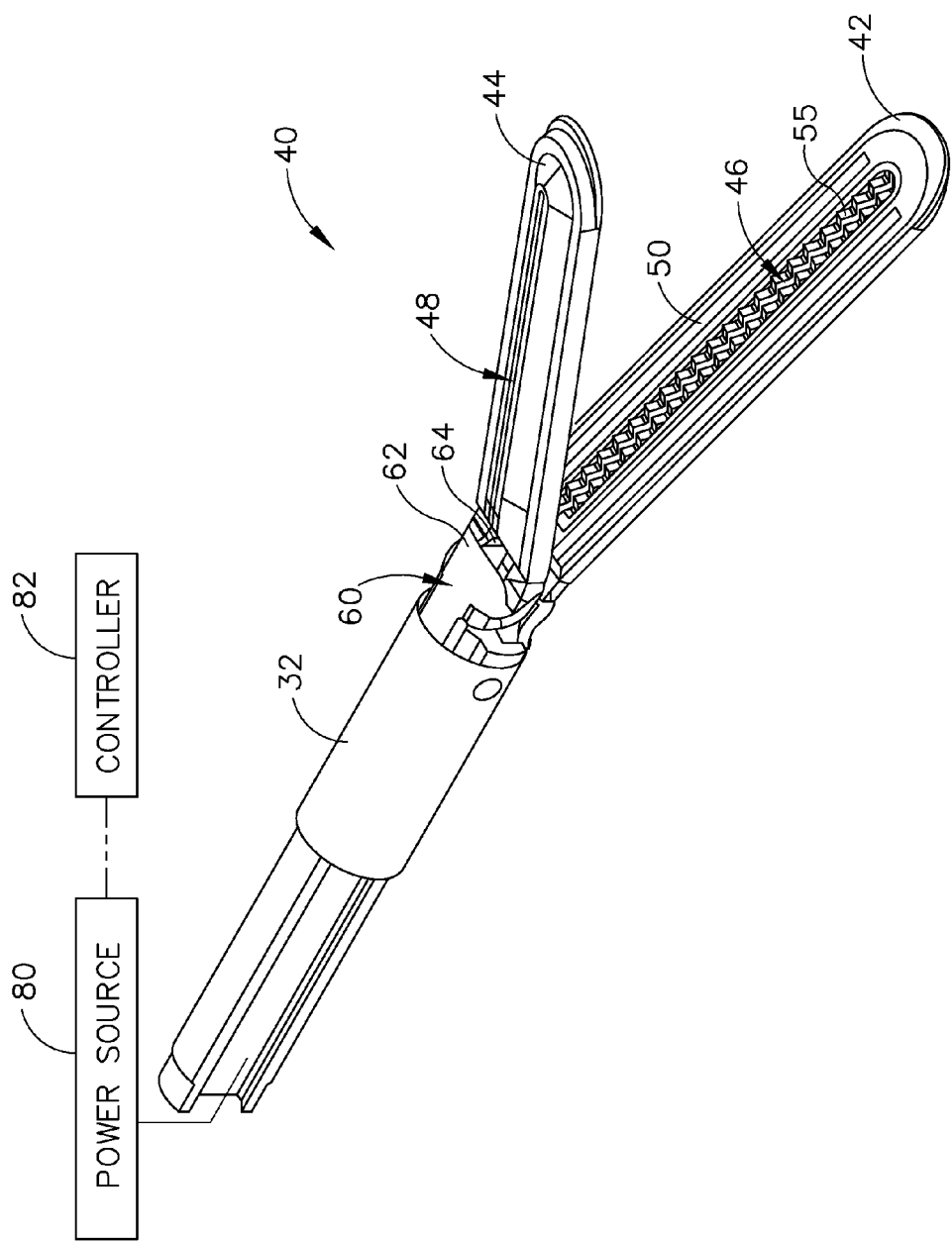
FIG. 2 depicts a perspective view of the end effector of the instrument of FIG. 1, in an open configuration.
Figure 3:
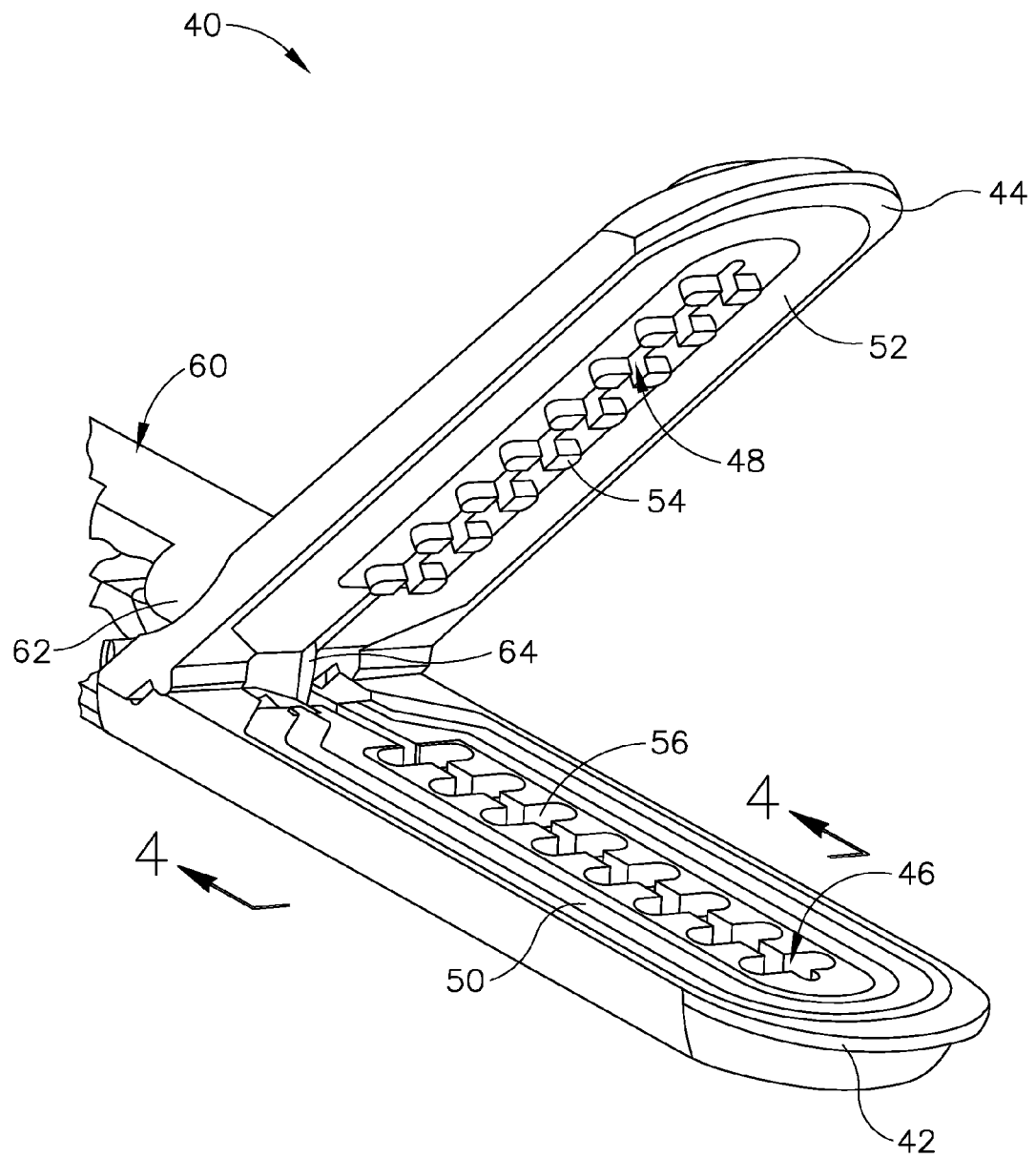
FIG. 3 depicts another perspective view of the end effector of the instrument of FIG. 1, in an open configuration.
Figure 4:
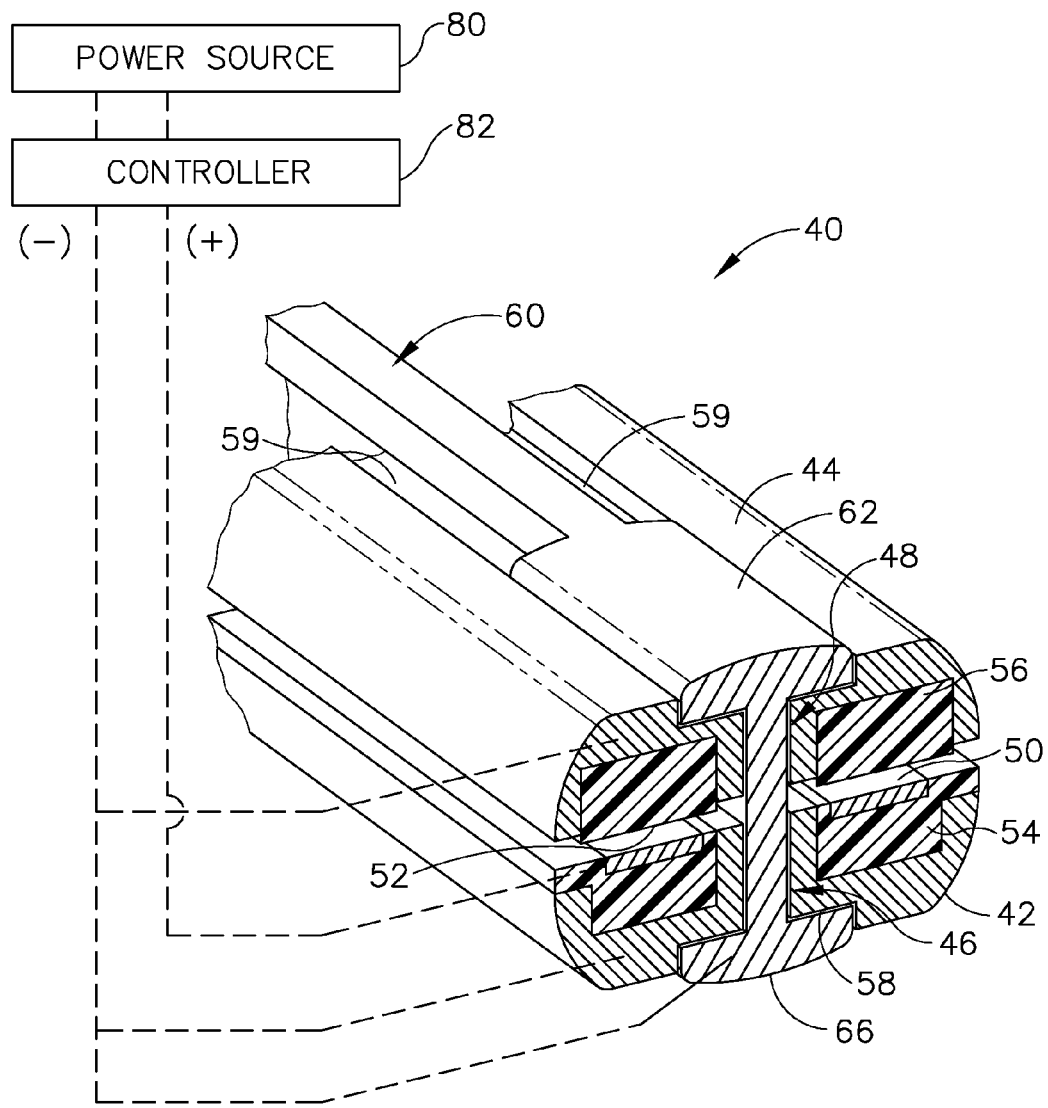
FIG. 4 depicts a cross-sectional end view of the end effector of FIG. 2, in a closed configuration and with the blade in a distal position, taken along line 4-4 of FIG. 3.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). These conductors are coupled with electrical source (80) and a controller (82) via a cable (84), which extends proximally from handpiece (20). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

By way of example only, power source (80) and/or controller (82) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued Jun. 23, 2015, the disclosure of which is incorporated by reference herein. Other suitable configurations for power source (80) and controller (82) will be apparent to those of ordinary skill in the art in view of the teachings herein.

As best seen in FIG. 4, the lower side of first jaw (42) includes a longitudinally extending recess (58) adjacent to slot (46); while the upper side of second jaw (44) includes a longitudinally extending recess (59) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. In other words, it should be understood that serrations may be generally blunt or otherwise atraumatic. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. In some versions, a proximal end of firing beam (60) is secured to a firing tube or other structure within shaft (30); and the firing tube or other structure extends through the remainder of shaft (30) to handpiece (20) where it is driven by movement of trigger (24). Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (44) when firing beam (60) is retracted to a proximal position and to hold jaw (44) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

Figure 5:
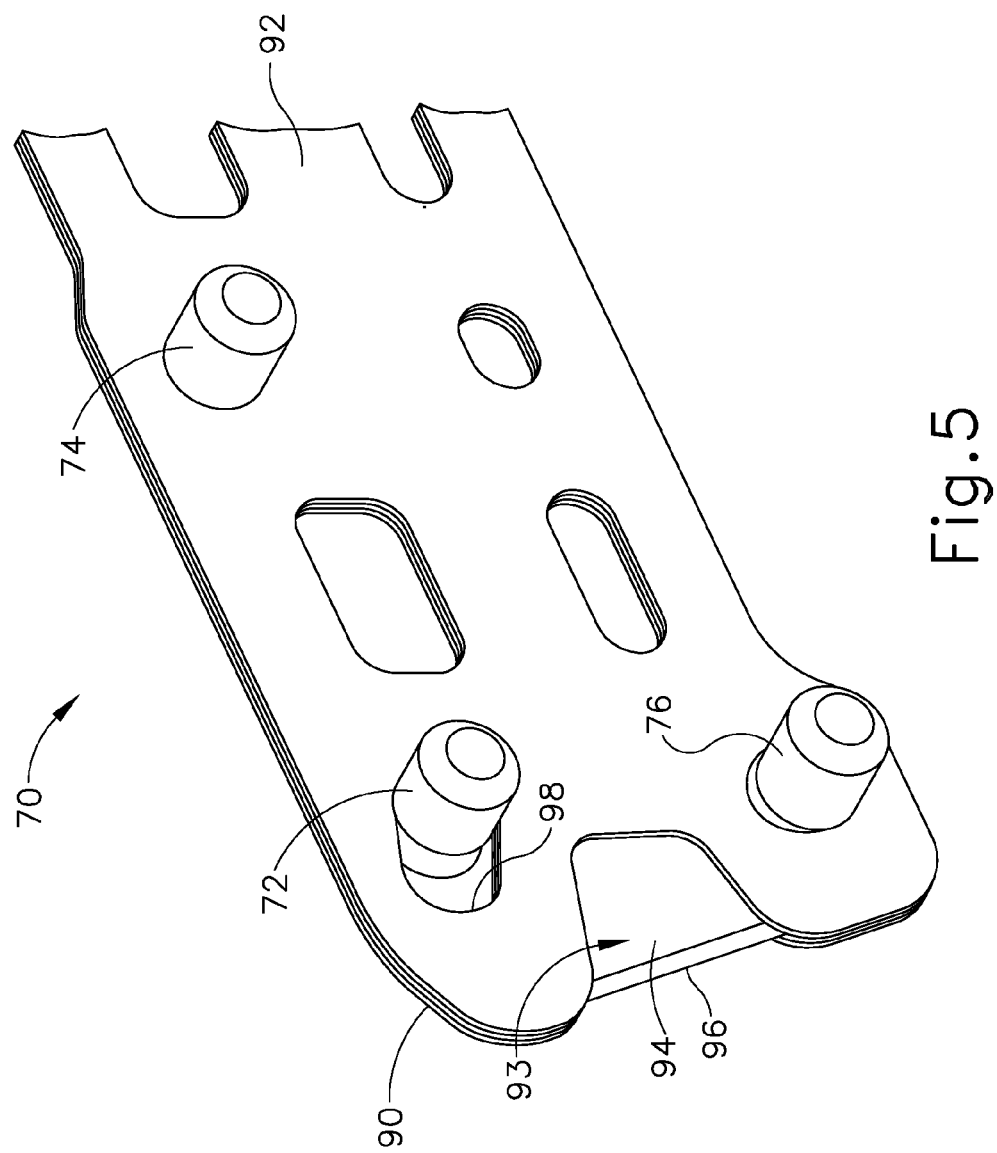
FIG. 5 depicts a partial perspective view of the distal end of an exemplary alternative firing beam suitable for incorporation in the instrument of FIG. 1.

FIG. 5 shows an exemplary alternative firing beam (70), which may be readily substituted for firing beam (60). In this example, firing beam (70) comprises a blade insert (94) that is interposed between two beam plates (90, 92). Blade insert (94) includes a sharp distal edge (96), such that blade insert (94) will readily sever tissue that is captured between jaws (42, 44). Sharp distal edge (96) is exposed by a proximally extending recess (93) formed in plates (90, 92). A set of pins (72, 74, 76) are transversely disposed in plates (90, 92). Pins (72, 74) together effectively serve as substitutes for upper flange (62); while pin (76) effectively serves as a substitute for lower flange (66). Thus, pins (72, 74) bear against channel (59) of jaw (44), and pin (76) bears against channel (58) of jaw (42), as firing beam (70) is translated distally through slots (46, 48). Pins (72, 74, 76) of the present example are further configured to rotate within plates (90, 92), about the axes respectively defined by pins (72, 74, 76). It should be understood that such rotatability of pins (72, 74, 76) may provide reduced friction with jaws (42, 44), thereby reducing the force required to translate firing beam (70) distally and proximally in jaws (42, 44). Pin (72) is disposed in an angled elongate slot (98) formed through plates (90, 92), such that pin (72) is translatable along slot (98). In particular, pin (72) is disposed in the proximal portion of slot (98) as firing beam (70) is being translated distally. When firing beam (70) is translated proximally, pin (72) slides distally and upwardly in slot (98), increasing the vertical separation between pins (72, 76), which in turn reduces the compressive forces applied by jaws (42, 44) and thereby reduces the force required to retract firing beam (70). Of course, firing beam (70) may have any other suitable configuration. By way of example only, firing beam (70) may be configured in accordance with at least some of the teachings of U.S. Pub. No. 2012/0083783, now U.S. Pat. No. 8,888, 809, the disclosure of which is incorporated by reference herein.

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary End Effector with Moveable Hinge

In some instances, an operator may use instrument (10) to cut and seal a vessel. Depending on characteristics of the vessel and the positioning of end effector (40), there may be a tendency for jaws (42, 44) to drive the vessel distally, effectively "milking" the tissue vessel away from pivotal coupling (43). This may result in a bunching of tissue on the distal side of the vessel, wherein the compression by jaws (42, 44) may be reduced. This may ultimately result in non-uniform tissue compression, which may in turn result in a poor tissue seal. This kind of compression action may be addressed by using a floating hinge configuration, which may ultimately enable a greater distribution of compression forces on the tissue, thereby providing a better seal of the tissue. One merely illustrative example of a floating hinge configuration that may be incorporated into instrument (10) will be described in greater detail below; while other examples will be apparent to those of ordinary skill in the art in view of the teachings herein.

Figure 7A:
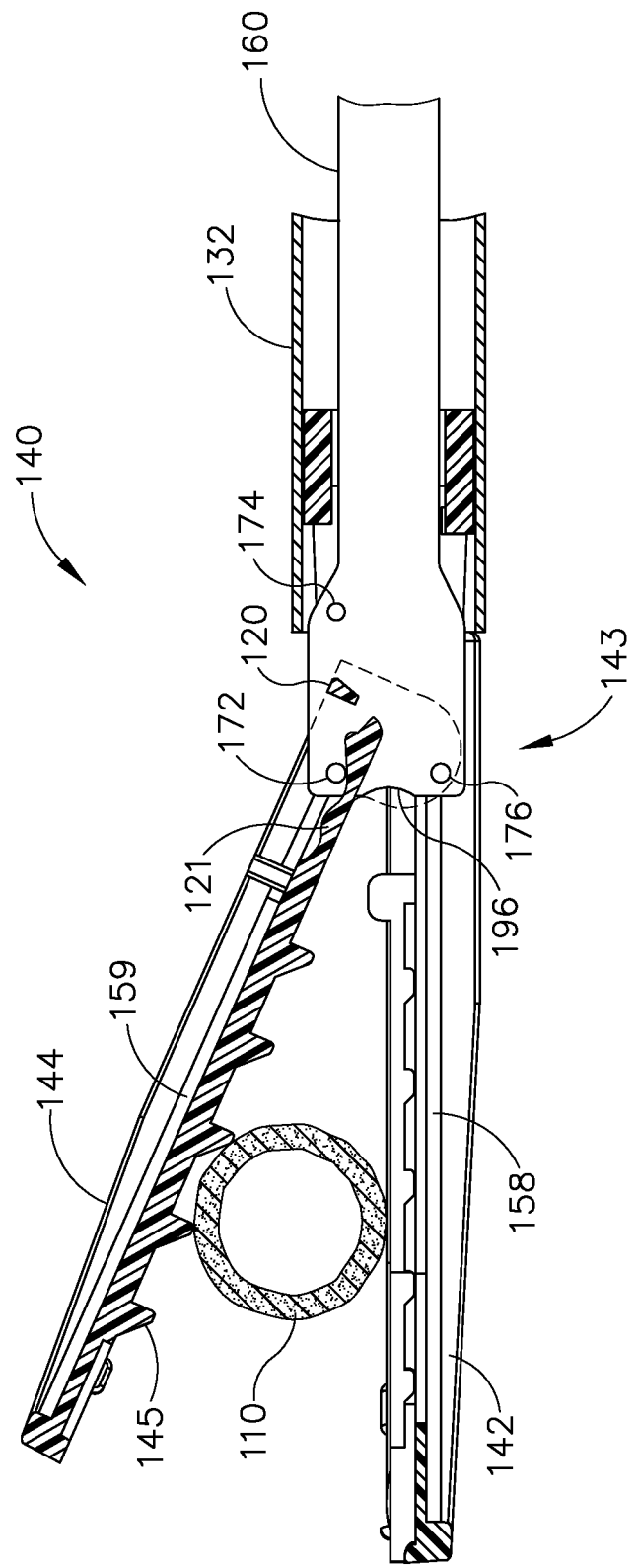
FIG. 7A depicts side, cross sectional view of the end effector of FIG. 6 an open position, with the firing beam in a first position.
Figure 7B:
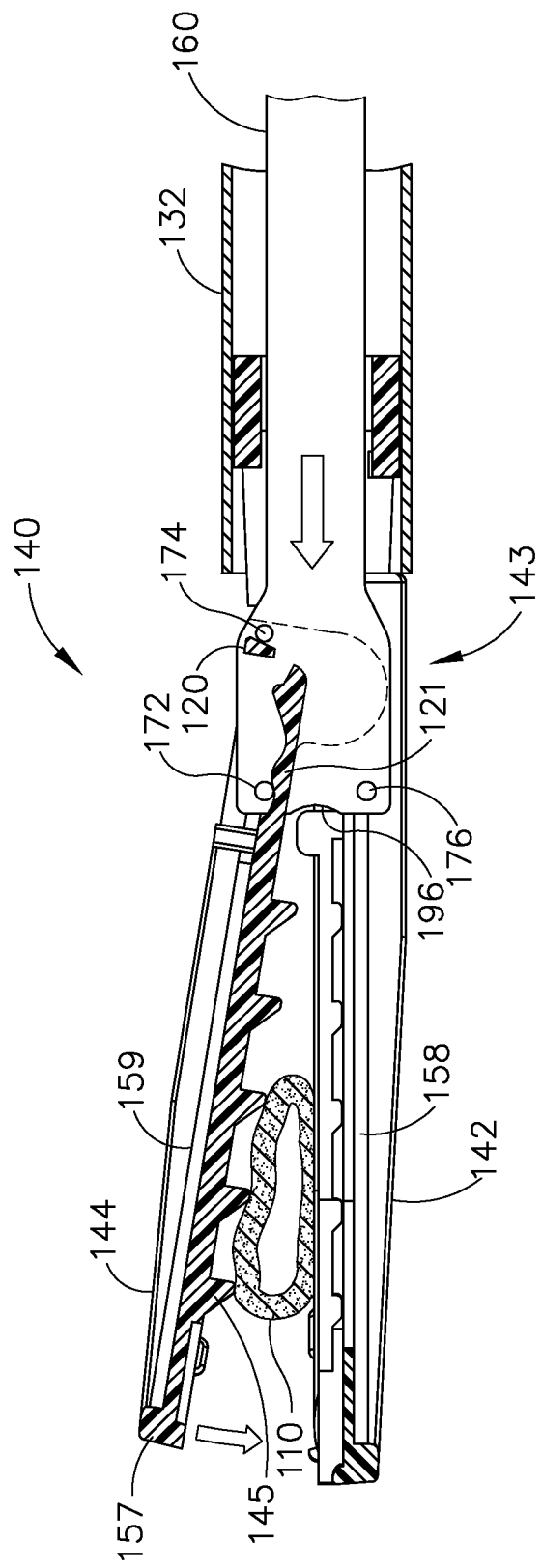
FIG. 7B depicts a side, cross sectional view of the end effector of FIG. 6 closing on a vessel, with the firing beam advanced to a second position.
Figure 7C:
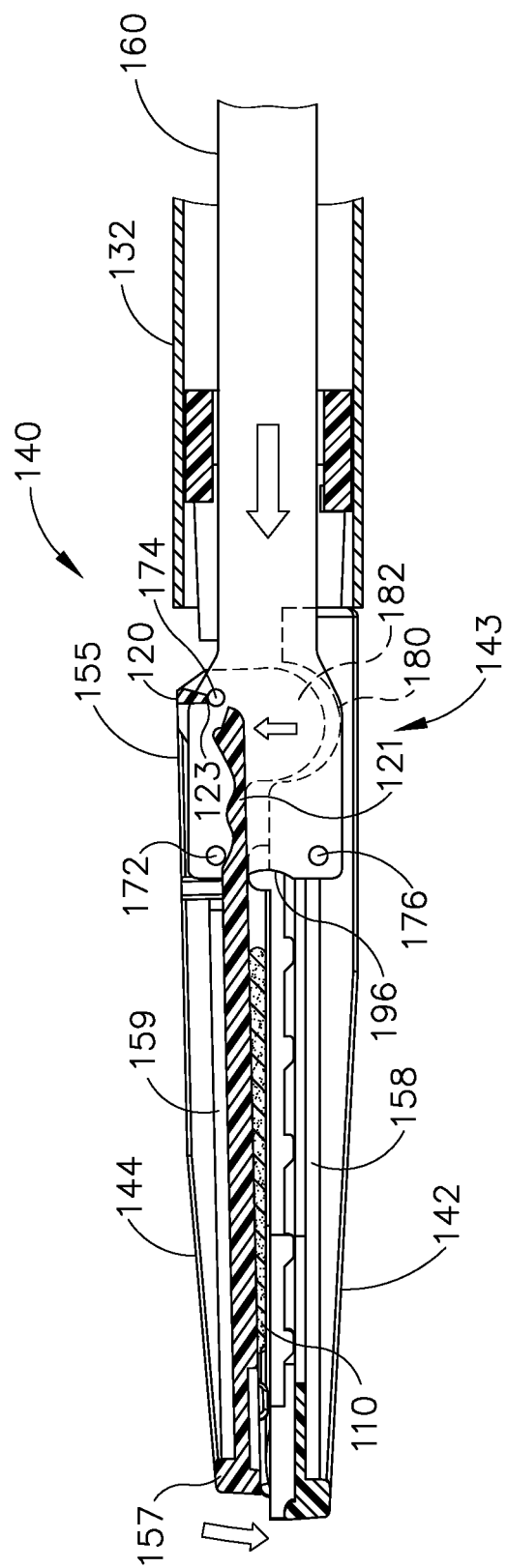
FIG. 7C depicts a side, cross sectional view of the end effector of FIG. 6 closed on a vessel and the hinge raised, with the firing beam advanced to a third position.
Figure 7D:
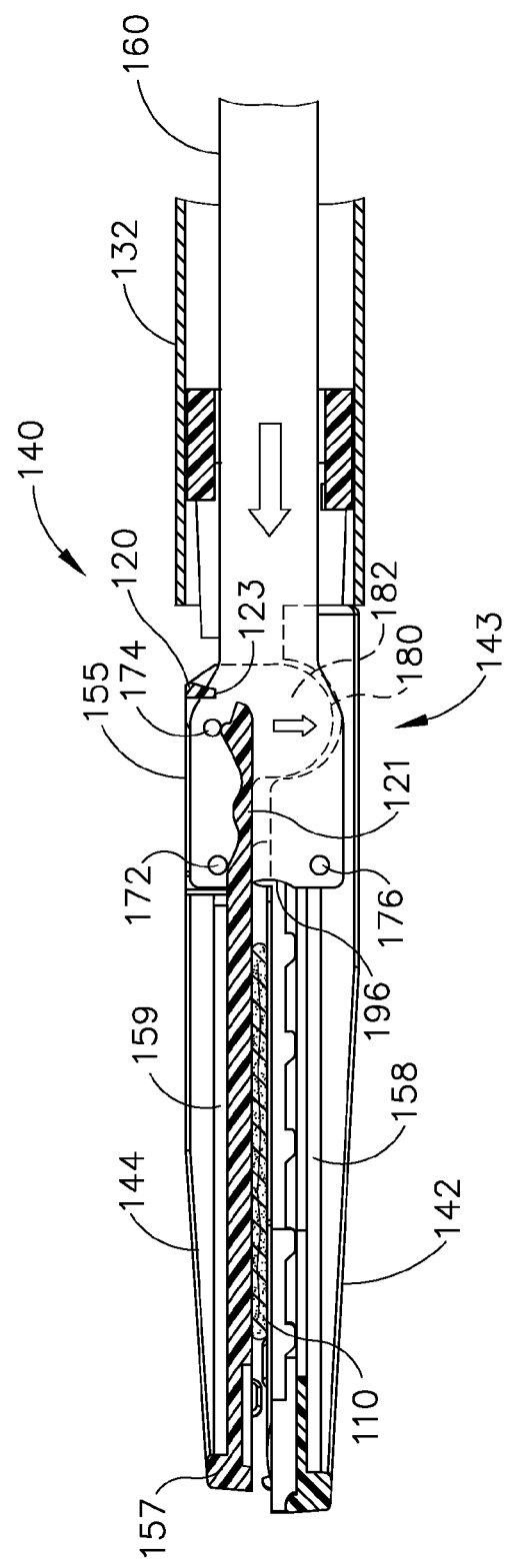
FIG. 7D depicts a side, cross sectional view of the end effector of FIG. 6 closed on a vessel and the hinge lowered, with the firing beam advanced to a fourth position.
Figure 7E:
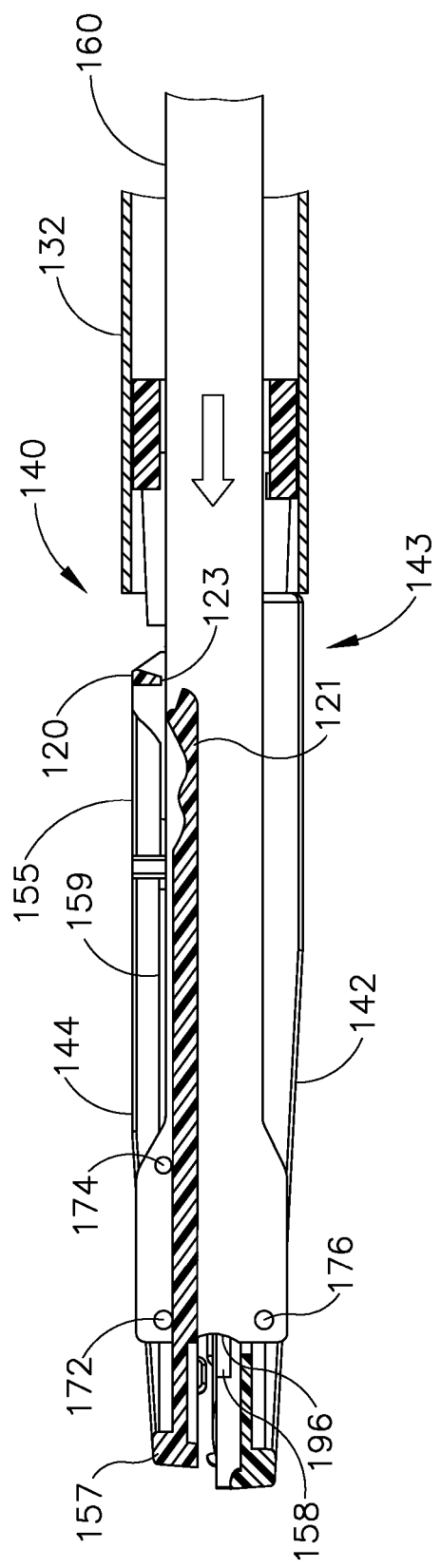
FIG. 7E depicts a side, cross sectional view of the end effector of FIG. 6 closed and with the firing beam fully advanced to a fifth position.

As shown in FIGS. 6-7E, end effector (140) of the present example comprises a first jaw (142) and a second jaw (144) that are coupled at a pivotal coupling (143). It should be understood that end effector (140) may readily serve as a substitute for end effector (40) described above. Except as otherwise set forth below, end effector (140) may be configured and operable just like end effector (40).

First jaw (142) is operable to pivot in relation to second jaw (144) through pivotal coupling (143). In the present example, the pivot point provided by pivotal coupling (143) is not fixed. In particular, the pivot point may travel vertically with second jaw (144) in relation to first jaw (142). This enables a rocking action of second jaw (144) in relation to first jaw (142) as will be described in greater detail below. During this rocking, second jaw (144) first defines an oblique angle with first jaw (142) at a proximal vertex; then later second jaw (144) defines an oblique angle with first jaw (142) at a distal vertex. Pivotal coupling (143) comprises a hinge (180) and a seat (182). Hinge (180) is defined by second jaw (144) while seat (182) is defined by first jaw (142). Hinge (180) is operable to pivot about seat (182) to enable pivoting of second jaw (144) in relation to first jaw (142). Hinge (180) is also operable to travel upwardly out of seat to enable vertical displacement of the proximal end of second jaw (144) in relation to first jaw (142).

It will be understood that a vessel may be placed between first jaw (142) and second jaw (144). For instance, end effector (140) may be maneuvered through tissue in order to position end effector (140) such that first jaw (142) and second jaw (144) can clamp on the vessel. Thereafter, first jaw (142) closes upon the vessel, and a firing beam (160) may then be advanced through end effector (140) to compress and cut the vessel as will be described in further detail below in FIGS. 7A-E. It will be appreciated that while the description below contemplates using end effector (140) on vessel tissue, end effector (140) may be used with any suitable type of tissue as will be apparent to one of ordinary skill in the art in view of the teachings herein.

FIG. 7A shows a cross sectional view of end effector (140). In addition to first jaw (142) and second jaw (144), end effector (140) comprises a firing beam (160) where that is translatable through an outer sheath (132). Firing beam (160) has integral, laterally projecting pins (172, 174, 176). It will be appreciated that pins (172, 174, 176) are substantially similar to pins (72, 74, 76) of FIG. 5. Firing beam (160) also comprises a sharp distal edge (196) substantially similar to sharp distal edge (96) of FIG. 5. With tissue such as vessel tissue (110) placed between first jaw (142) and second jaw (144), firing beam (160) may advance distally to close first jaw (142) toward second jaw (144), thereby compressing tissue (110) between jaws (142, 144). Furthermore, as firing beam (160) advances through jaws (142, 144), sharp distal edge (196) severs the tissue (110) clamped between jaws (142, 144). It will be appreciated that jaws (142, 144) may include electrode surfaces substantially similar to electrode surfaces (50, 52) shown in FIG. 3 to enable end effector (140) to seal tissue, prior to, during, and/or after firing beam (160) advances.

First jaw (142) defines a longitudinally extending recess (158). Longitudinally extending recess (158) is shaped to accommodate lower pin (176) as firing beam (160) advances. Firing beam (160) may be driven such that firing beam (160) advances longitudinally along first jaw (142). At least with respect to first jaw (142), as firing beam (160)

advances, lower pin (176) travels along longitudinally extending recess (158). First jaw (142) may in some instances include visual indicators (lines, markings, circles, ticks, etc.) configured to indicate to the user whether tissue (110) is properly positioned on first jaw (142).

Second jaw (144) also comprises a longitudinally extending recess (159). Longitudinally extending recess (159) is shaped to accommodate distal pin (172) and proximal pin (174). As firing beam (160) is driven, distal pin (172) and proximal pin (174) travel along longitudinally extending recess (159) of second jaw (144). Further detail regarding advancing firing beam (160) along second jaw (144) will be described in below. Second jaw (144) further comprises teeth (145). Teeth (145) are operable to promote gripping of tissue (110). It will be appreciated that in some instances, teeth (145) may be omitted entirely.

Second jaw (144) further comprises a cross beam (120) and an undulating portion (121). Cross beam (120) and undulating portion (121) are operable to engage firing beam (160) as firing beam (160) advances along end effector (140). In particular, cross beam (120) is operable to engage proximal pin (174), and undulating portion (121) is operable to engage distal pin (172) as well as proximal pin (174). FIG. 7A shows end effector (140) in preparation for firing to clamp, seal, and cut tissue (110) placed between first jaw (142) and second jaw (144). Firing beam (160) is in a first position. Proximal pin (174) is positioned proximally in relation to cross beam (120) and distal pin (172) is seated in undulating portion (121). As also seen in FIG. 7A, tissue (110) is not in any state of compression between open jaws (142, 144).

FIG. 7B shows end effector (140) closing on tissue (110). In particular, firing beam (160) has advanced to a second position. In the second position, distal pin (172) has advanced distally further along undulating portion (121). Since distal pin (172) and lower pin (176) advance in a parallel manner along longitudinally extending recesses (158, 159), second jaw (144) is driven toward first jaw (142) by distal pin (172), thereby squeezing tissue (110). This movement involves second jaw (144) generally pivoting toward first jaw (142) about pivotal coupling (143). Teeth (145) promote gripping between second jaw (144) and tissue (110). As second jaw (144) closes against first jaw (142), tissue (110) is squeezed toward distal tip (157) of second jaw (144).

FIG. 7C shows end effector (140) further closed on tissue (110). In particular, firing beam (160) has advanced further to a third position. Distal pin (172) has advanced further along undulating portion (121) and has almost cleared undulating portion (121). As proximal pin (174) encounters cross beam (120), the slightly angled shape of cross beam (120) causes proximal pin (174) to traverse cross beam (120) on the underside (123) of cross beam (120). As proximal pin (174) traverses underside (123), proximal pin (174) drives cross beam (120) upwardly, which lifts hinge (180) slightly from seat (182). It will be appreciated that hinge (180) may be pivotally coupled to seat (182) by an elongated slot or any other suitable means to facilitate movement of hinge (180) in a direction perpendicular or generally perpendicular to the longitudinal axis of firing beam (160). It will be understood that while the illustrated version contemplates hinge (180) lifting generally perpendicularly to seat (182) as proximal pin (174) traverses underside (123) of cross beam (120), hinge (180) may lift in any suitable oblique angle in relation to longitudinal axis of firing beam (160) as would be apparent to one of ordinary skill in the art in view of the teachings herein.

As hinge (180) lifts from seat (182), pin (172) acts as a fulcrum against second jaw (144) such that distal tip (157) of second law (144) is tipped downwardly. As a result, tissue (110) is squeezed proximally toward pivotal coupling (143). It will be appreciated that squeezing tissue (110) distally as seen in FIG. 7B and then proximally as seen in FIG. 7C may ultimately promote more consistent compression across the tissue (110). In other words, instead of tissue (110) being squeezed in a wedge-like manner and "milked" distally, tissue (110) may be squeezed in a more parallel or flat manner due to the alternating squeezing of tissue (110) distally and then proximally as seen in FIGS. 7B-7C.

FIG. 7D shows end effector (140) fully closed on tissue (110) as firing beam (160) is advanced further distally. Proximal pin (174) has fully traversed cross beam (120) and bears against the first undulation of undulating portion (121). Accordingly, hinge (180) has lowered into seat (182), thereby lowering proximal portion (155) of second jaw (144). Distal pin (172) has cleared undulating portion (121). As also seen in the illustrated version, first jaw (142) and second jaw (144) have straightened out, such that first jaw (142) and second jaw (144) are parallel or substantially parallel. It will be appreciated that electrode surfaces, such as electrode surfaces (50, 52) shown in FIG. 3, in first jaw (142) and second jaw (144) may be energized to seal tissue (110) at this stage. However it will be appreciated that the electrode surfaces may be energized at any suitable time as would be apparent to one of ordinary skill in the art in view of the teachings herein.

FIG. 7E shows firing beam (160) fully advanced distally. Pins (172, 174) have fully traversed longitudinally extending recess (159). Pin (176) has fully traversed longitudinally extending recess (158). Furthermore, sharp distal edge (196) has advanced fully to sever tissue (110). Thereafter, tissue (110) is released from jaws (142, 144). In particular, firing beam (160) may be retracted proximally to allow second jaw (144) to unclamp from first jaw (142). Pin (172) may assist in driving second jaw (144) to the open position as soon as firing beam (160) reaches the proximal position shown in FIG. 7A. Alternatively, any other suitable means for releasing second jaw (144) from first jaw (142) may be used as will be apparent to one of ordinary skill in the art in view of the teachings herein.

III. Exemplary End Effector with Cylindraceous Electrode Features

Figure 8:
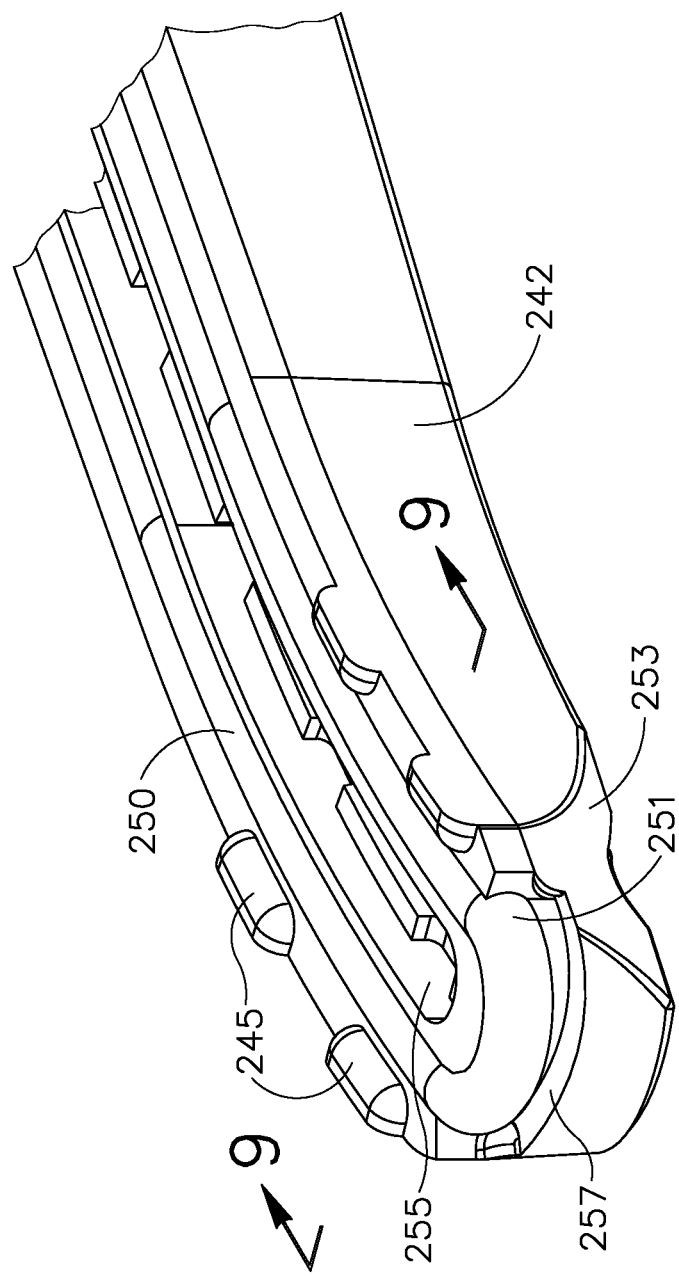
FIG. 8 depicts a perspective view of a first jaw of another exemplary alternative end effector that may be incorporated into the electrosurgical medical instrument of FIG. 1.

In some instances, it may be desirable to use an electrode having different features than those previously described above. For instance, it may be desirable for an electrode to contact tissue over a curved surface instead of over a flat surface. FIG. 8 shows an exemplary jaw (242) that may be readily incorporated into an end effector such as end effector (140) shown in FIG. 6. It will be appreciated that jaw (242) may be used in place of first jaw (142) and/or second jaw (144) seen in FIG. 6. Jaw (242) of the present example comprises an electrode (250) extending through jaw (242). Furthermore, jaw (242) comprises a plurality of teeth (245) lined along the exterior of jaw (242). Jaw (242) also defines a slot (255) that extends longitudinally along jaw (242), and jaw (242) defines a cutout (253) within jaw (242). Jaw (242) comprises a curved shape. It will be appreciated that in some versions, a curved or straight shape for jaw (242) may be used. However, any suitable shape for jaw (242) may be used as would be apparent to one of ordinary skill in the art in view of the teachings herein.

Figure 9:
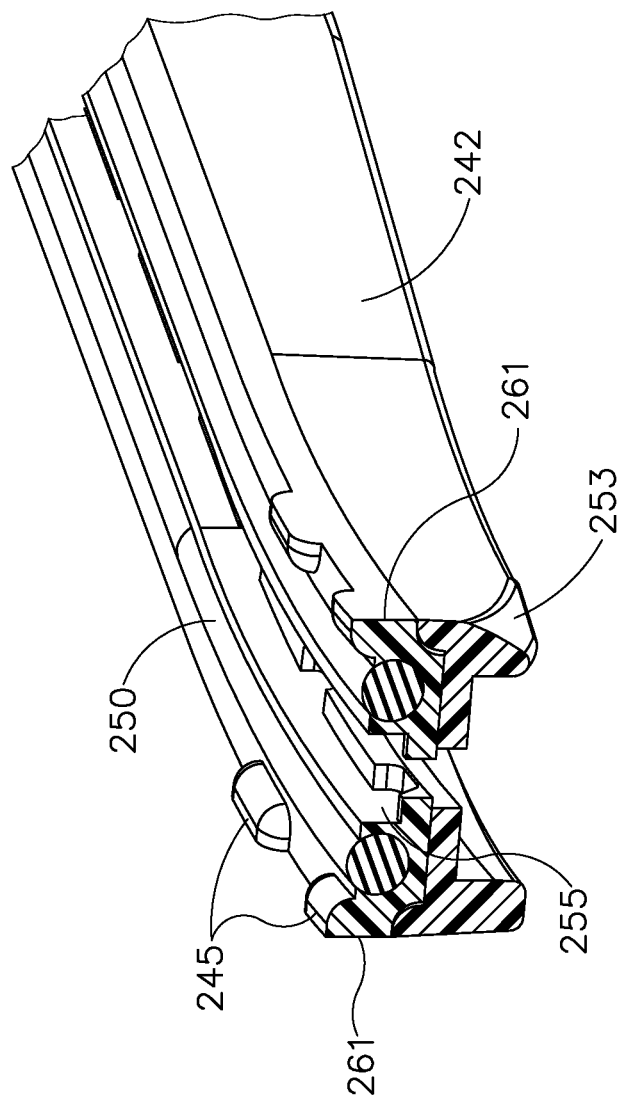
FIG. 9 depicts a perspective, cross sectional view of the first jaw of FIG. 8, taken along the 9-9 of FIG. 8.

Electrode (250) in the exemplary version has a cylindrical shape and wraps around the distal tip (257) of jaw (242) to form a curved portion (251). FIG. 9 shows a cross section of electrode (250) showing the cylindrical shape of electrode (250). It will be appreciated that while the exemplary version shows electrode (250) with a circular cross section, other rounded cross sections may be used as would be apparent to one of ordinary skill in the art in view of the teachings herein. For instance, in some versions an elliptical, a rounded rectangular cross section, or any other suitable cross section may be used as would be apparent to one of ordinary skill in the art in view of the teachings herein. It will be appreciated that due to rounded cross section of electrode (250), the area of compression against tissue held by jaw (242) may be narrower than if electrode (250) had a flat tissue contact surface. Furthermore, electrode (250) may be positioned closer to slot (255) and away from the outer surface (261) of jaw (242). For instance, the distance between electrode (250) and slot (255) may be smaller than the distance between electrode (250) and outer surface (261). As a result, when electrode (250) is energized, it will be appreciated that reduced thermal energy may spread to outer surface (261) due in part to the positioning of electrode (250) closer to slot (255) as well as the rounded cross section of electrode (250).

In some instances, it may be desirable to apply thermal energy to a portion of tissue that may not be positioned between jaw (242) and another jaw. As mentioned above, jaw (242) includes a cutout portion (253). Cutout portion (253) exposes a portion of electrode (250). This portion of electrode (250) is exposed even when another jaw (e.g., jaw (44)) is closed against jaw (242). As a result, the user may press the exposed electrode (250) onto tissue while electrode (250) is energized and while jaws are closed, thereby allowing the user to weld a portion of tissue with electrode (250). This may be done when using an end effector incorporating electrode (242) in a blunt dissection and/or in other kinds of acts. Cutout portion (253) is near distal tip (257) in the present example, it will be appreciated that any suitable portion of jaw (242) may be cutout or thinned to expose or reduce the space between electrode (250) and the outermost surface of jaw (242).

Curved portion (251) extends to distal tip (257); or in some versions may extend just short of distal tip (257). Furthermore, in the exemplary version, electrode (250) follows a curved path that follows along the contour of jaw (242). It will be appreciated that in the event that jaw (242) curved differently or were straight, electrode (250) may also follow the curvature of jaw (242).

A plurality of teeth (245) line the exterior of jaw (242) and promote gripping of tissue by jaw (242). While four teeth (245) are shown in the present example, it should be understood that any suitable number of teeth (245) may be used as would be apparent to one of ordinary skill in the art in view of the teachings herein. For instance, 1, 2, 3, 5, 6 or more teeth (245) may be used. Furthermore, in the exemplary version, teeth (245) are positioned with an equal number on either side of slot (255) and are positioned in a parallel manner along jaw (242). However, it will be understood that any suitable number of teeth (245) may be placed on either side of slot (255) and may be placed in an offset manner in relation to each other or in any other arrangement. Other suitable ways of positioning teeth (245) will be apparent to one of ordinary skill in the art in view of the teachings herein. Furthermore, teeth (245) in the exemplary version each have a flat exterior facing portion and a rounded interior facing portion. However, it will be understood that teeth (245) may have any suitable atraumatic shape as would be apparent to one of ordinary skill in the art in view of the teachings herein.

Figure 10:
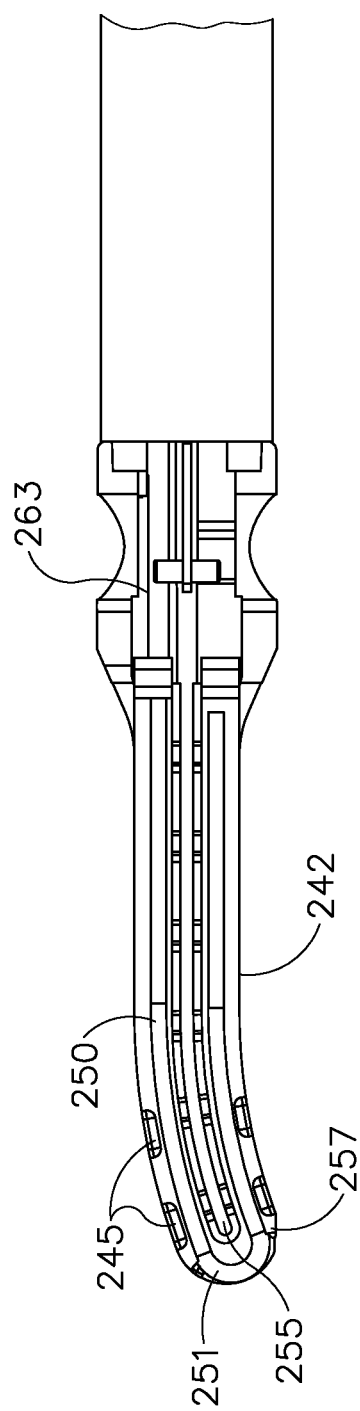
FIG. 10 depicts a top, plan view of the first jaw of FIG. 8, showing the electrode along the first jaw.

FIG. 10 shows a top view of jaw (242). As shown, electrode (250) is in communication with an activation rod (263). Activation rod (263) is operable to communicate electrical power to electrode (250). In some versions, activation rod (263) is overmolded within jaw (242). In addition or in the alternative, activation rod (263) may be encapsulated in PTFE, heat resistant nylon, and/or any other suitable material(s). When the user is ready to energize electrode (250), energy flows through activation rod (263) to deliver energy to electrode (250), without also delivering energy to the exterior of jaw (242).

IV. Exemplary End Effector with Spring Leverage

Figure 11:
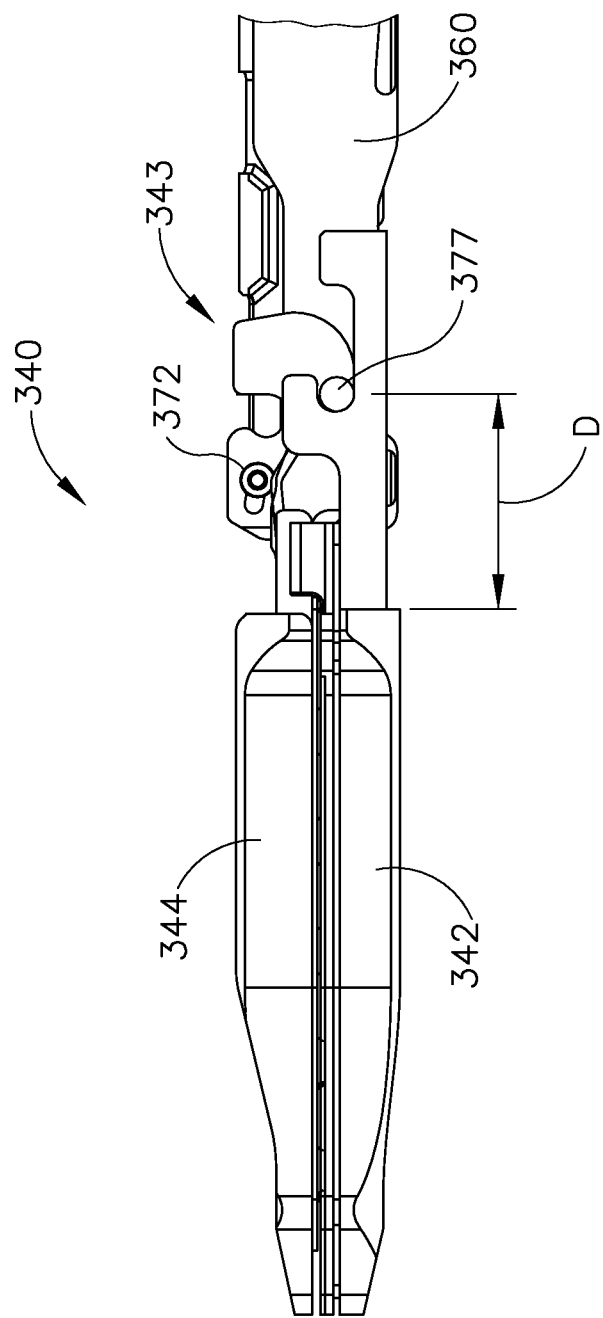
FIG. 11 depicts a side, elevation view of another exemplary alternative end effector that may be incorporated into the electrosurgical medical instrument of FIG. 1.

It may be desirable to enhance the clamping strength provided by jaws (42, 44) of end effector (40), particularly at a stage where firing beam (60) has been advanced distally enough to close jaws (42, 44) but not distally enough to sever tissue clamped between jaws (42, 44). One way to do this would be to incorporate a stiff resilient member into jaw (44). Such a stiff resilient member may engage firing beam (60) to drive jaw (44) toward jaw (42) earlier during the advancement stroke; and may then yield to permit firing beam (60) to complete a full advancement stroke. One merely illustrative way in which this could be carried out is shown in FIGS. 11-12B and is described in greater detail below. Other suitable ways in which this could be carried out will be apparent to those of ordinary skill in the art in view of the teachings herein FIGS. 11-12B show an exemplary end effector (340) that may be readily incorporated into instrument (10) as a substitute for end effector (40). End effector (340) of this example comprises a first jaw (342), a second jaw (344), and a firing beam (360). It will be appreciated that first jaw (342) and second jaw (344) are substantially identical to jaws (142, 144, 42, 44) described above. First jaw (342) and second jaw (344) are coupled via pivotal coupling (343). Pivotal coupling (343) is operable to provide pivoting of second jaw (344) relative to first jaw (342). Pivotal coupling (343) comprises a pivot pin (377), which serves as the pivot point between first jaw (342) and second jaw (344). It will be appreciated that pivot pin (377) may be positioned through or below the longitudinal center of end effector (340). As shown in FIG. 11, a distance (D) represents the distance that firing beam (360) must travel prior to cutting tissue between first jaw (342) and second jaw (344). It will be appreciated that distance (D) may be any suitable length such as for instance approximately 0.36 inches. Of course, shorter and longer lengths for distance (D) may be used as will be apparent to those of ordinary skill in the art in view of the teachings herein.

Pivotal coupling (343) comprises a leaf spring (370) secured to a top portion of jaw (344). While a leaf spring (370) is used in the present example, it should be understood that any other suitable kind of resilient member (or resiliently biased member) may be used. Leaf spring (370) is resiliently biased to assume the bent profile shown in FIG. 12A. Second jaw (344) defines a distal engagement portion (371) and a proximal engagement portion (373). Distal engagement portion (371) receives a distal portion of leaf spring (370) and proximal engagement portion (373) is receives a proximal portion of leaf spring (370). In the present example, leaf spring (370) is secured to one of these portions (371, 373) but is slidable relative to the other portion (371, 373). Leaf spring (370) is configured to promote driving of second jaw (373) toward first jaw (370) such that second jaw (373) compresses sooner and more forcefully toward first jaw (370).

Figure 12A:
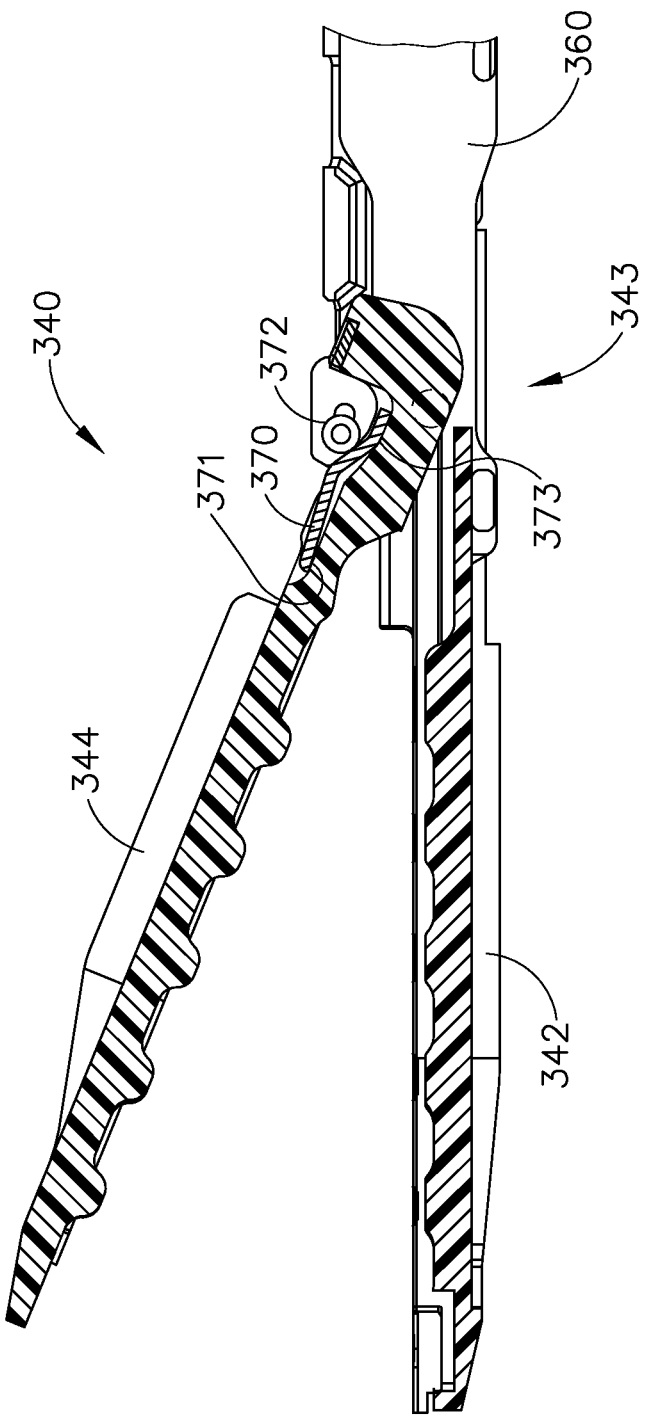
FIG. 12A depicts a side, cross sectional view of the end effector of FIG. 11 in an open position showing a jaw closing spring.
Figure 12B:
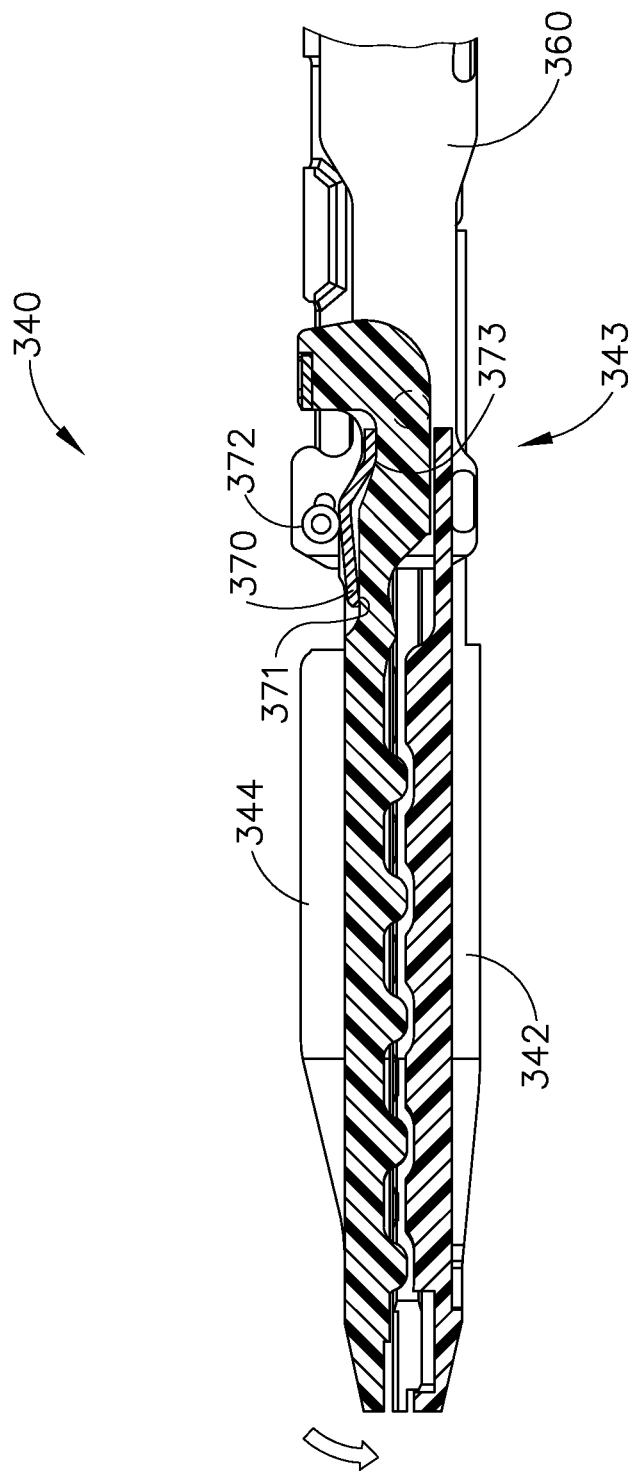
FIG. 12B depicts a side, cross sectional view of the end effector of FIG. 11 in a closed position with a firing beam partially advanced.
Figure 13:
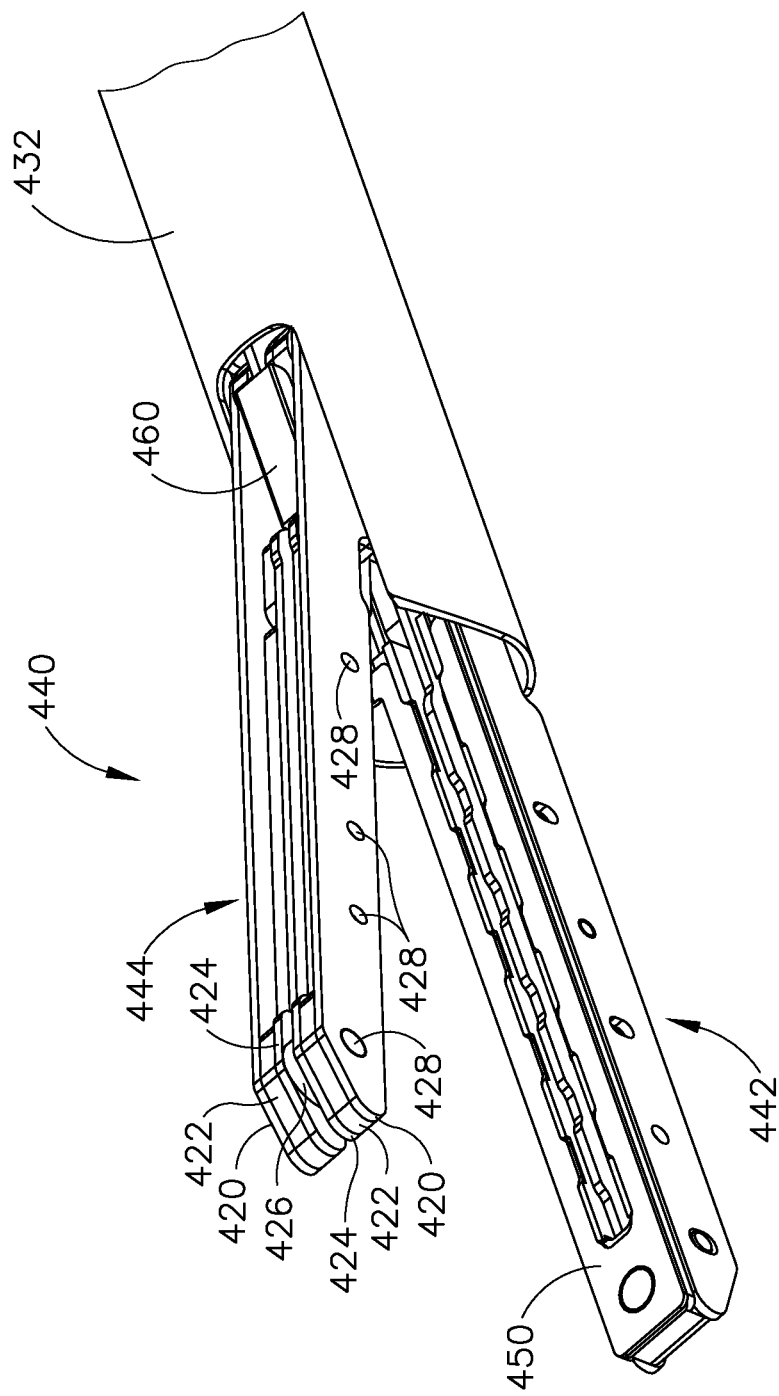
FIG. 13 depicts a top, perspective view of another exemplary alternative end effector that may be incorporated into the electrosurgical medical instrument of FIG. 1, having a layered construction.
Figure 14:
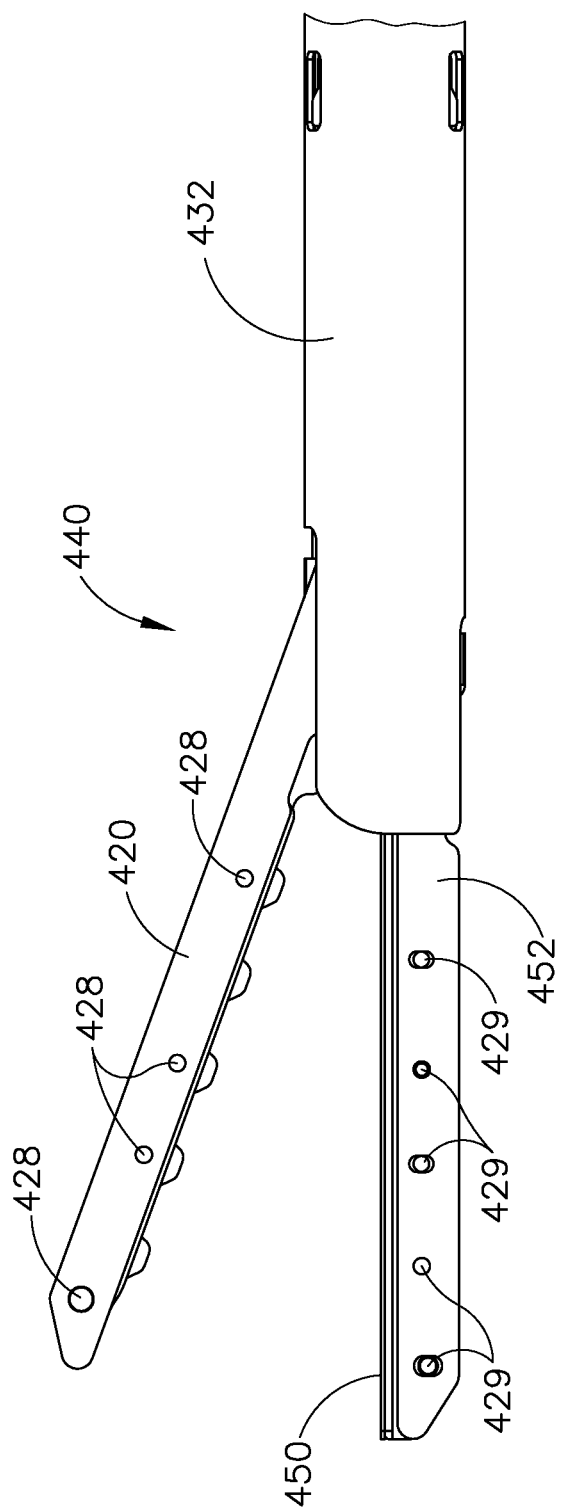
FIG. 14 depicts a side, elevation view of the end effector of FIG. 13.
Figure 15:
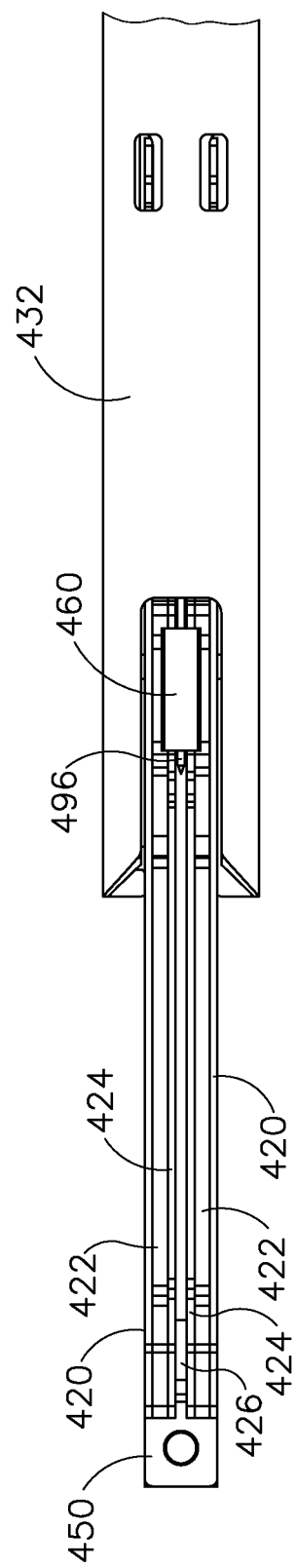
FIG. 15 depicts a top, plan view of the end effector of FIG. 13.

As seen in FIG. 12A, second jaw (344) is opened relative to first jaw (342). Firing beam (360) is in a refracted position. Leaf spring (370) is in a non-stressed configuration. However, a pin (372) of firing beam (360) is in contact with leaf spring (370). The proximally facing surface of leaf spring (370) provides a cam surface such that pin (372) will bear against leaf spring (370) as soon as firing beam (360) is advanced distally from the position shown in FIG. 12A. As pin (372) bears against leaf spring (370), the resulting camming action pivots jaw (344) toward jaw (342) about pin (377). In particular, pin (372) drives leaf spring (370) downwardly, and this downward force is transmitted to jaw (344) via distal engagement portion (371). Leaf spring (370) has enough stiffness to provide significant closure force to jaw (344) and to thereby provide significant clamping force against tissue positioned between jaws (342, 344). Thus, jaws (342, 344) are closed and tissue is clamped due to an interference relationship between pin (372) and leaf spring (370).

As firing beam (360) continues to advance distally, leaf spring (370) eventually deforms enough to allow pin (372) to clear leaf spring (370). FIG. 12B shows a transition state where pin (372) has just finished traversing the greatest interference region with leaf spring (370). After pin (372) has cleared leaf spring (370), pin (372) contacts an upper surface of jaw (344) and thereby maintains compression of tissue between jaws (342, 344) as firing beam (360) completes its distal advancement stroke. In some instances, additional leverage may be provided by pre-cambering a distal portion of second jaw (344) such that when second jaw (344) closes on first jaw (342), additional clamping leverage may be provided at the distal end of jaws (342, 344). For instance, tissue clamped between jaws (342, 344) may be subject to equal or substantially equal clamping force along the longitudinal length of jaws (342, 344).

V. Exemplary End Effector with Layered Construction

FIGS. 13-16 show another exemplary end effector (440) that may be readily incorporated into instrument (10) as a substitute for end effector (40). End effector (440) of this example comprises a first jaw (442) and a second jaw (444), each of which is formed by a set of layered pieces. End effector (440) further comprises an outer sheath (432) secured to the proximal end of jaws (442, 444) and a firing beam (460) that is operable to translate through jaws (442, 444). It will be appreciated that firing beam (460) and outer sheath (432) may be substantially similar to firing beam (160) and outer sheath (132) described above.

Figure 16:
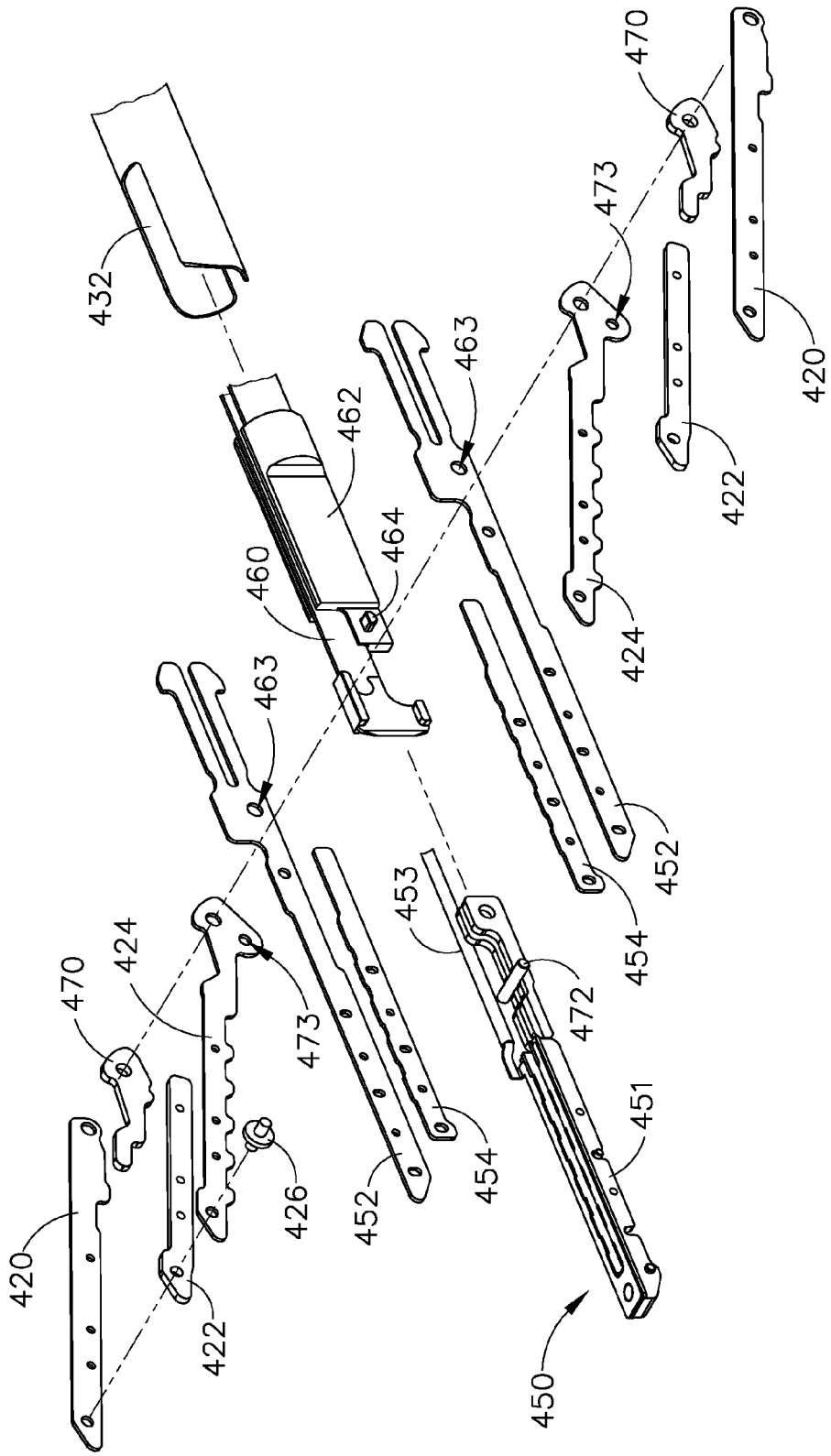
FIG. 16 depicts a perspective, exploded view of the end effector of FIG. 13.
Figure 17:
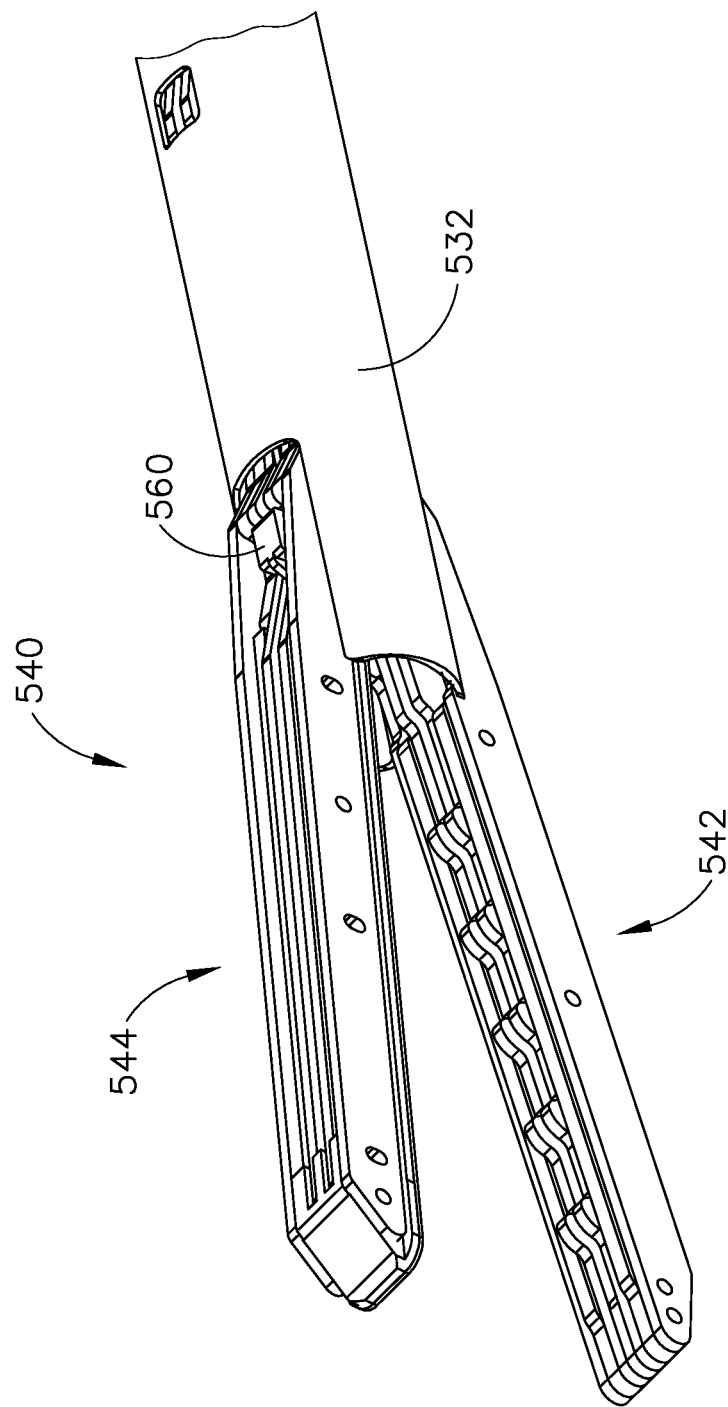
FIG. 17 depicts a top, perspective view of another exemplary alternative end effector that may be incorporated into the electrosurgical medical instrument of FIG. 1, having a layered construction and bilateral opening jaws.
Figure 18:
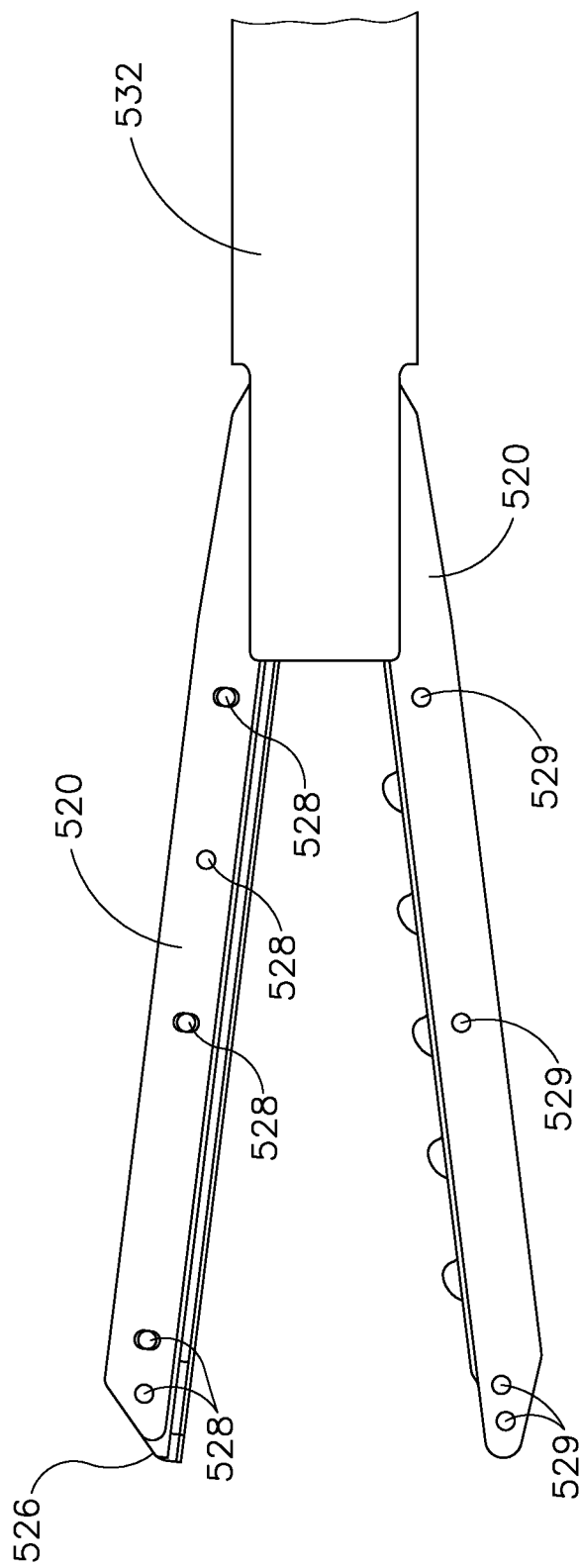
FIG. 18 depicts a side, elevation view of the end effector of FIG. 17.
Figure 19:
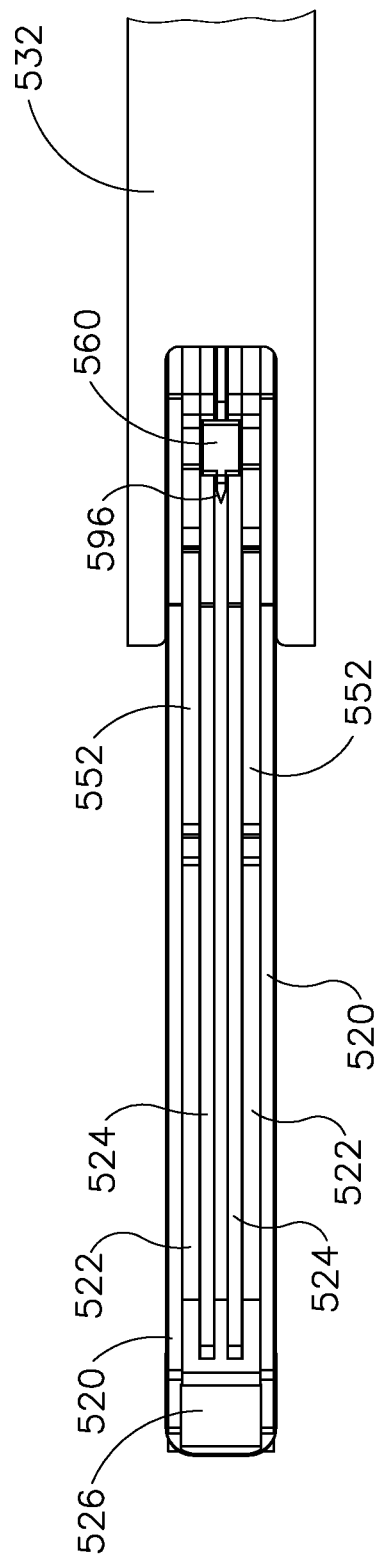
FIG. 19 depicts a top, plan view of the end effector of FIG. 17.

As best seen in FIG. 16, first jaw (442) comprises a lower jaw body (450), outer lower plates (452), and inner lower plates (454). Lower jaw body (450) comprises a molded plastic body with an overmolded conductive electrode surface (451). Of course, electrode surface (451) may have any other suitable construction. Electrode surface (451) is in communication with an activation conduit (453) that is operable to provide electrical energy to electrode surface (451). Inner lower plates (454) are interposed between outer lower plates (452) and lower jaw body (450). The proximal portions of outer lower plates (452) are fixedly secured to laterally projecting pins (464) of a ground frame (462), which is fixedly secured to outer sheath (432). Pins (464) are disposed in proximal openings (463) of outer lower plates (452).

Outer lower plates (452), inner lower plates (454), and lower jaw body (450) may be secured together through welding and/or any other suitable binding process. Lower jaw body (450), outer lower plates (452), and inner lower plates (454) comprise a plurality of lower openings (429). In some versions, plurality of lower openings (429) may be operable to receive pins, rivets, and/or other suitable components for holding lower jaw body (450), outer lower plates (452), and inner lower plates (454) together. In some versions, pins are disposed in openings (429) only to hold components of first jaw (442) in alignment during a welding process or other bonding process, such that the pins are removed after the welding/bonding process is complete.

In the present example, outer lower plates (452) are formed of metal while inner lower plates (454) are formed of plastic. Lower plates (454) are configured and positioned such that lower plates (454) will not come into contact with firing beam (460). Other suitable materials, configurations, and arrangements will be apparent to those of ordinary skill in the art in view of the teachings herein.

Second jaw (444) comprises outer plates (420), intermediate plates (422), and inner plates (424). Intermediate plates (422) are interposed between outer plates (420) and inner plates (424). Pivot supports (470) are also interposed between outer plates (420) and inner plates (424). Pivot supports (470) are thus coplanar with intermediate plates (422). Inner plates (425) include pivot openings (473). A pivot pin (472) is disposed through pivot openings (473) such that second jaw (444) is pivotable about pivot pin (472). A spacer (426) is interposed between inner plates (424) and is configured to maintain a lateral spacing between inner plates (424). In particular, spacer (426) is operable to provide sufficient clearance between inner plates (424) such that firing beam (460) can advance between inner plates (424).

Outer plates (420), intermediate plates (422), inner plates (424), and pivot supports (470) may be secured together through welding and/or any other suitable binding process. Outer plates (420), intermediate plates (422), inner plates (424), and pivot supports (470) form a plurality of upper openings (428) extending transversely through outer plates (420), intermediate plates (422), inner plates (424), and pivot supports (470). In some versions, upper openings (428) may be configured to receive pins, rivets, and/or other suitable components for holding outer plates (420), intermediate plates (422), inner plates (424), and pivot supports together. In some versions, pins are disposed in openings (428) only to hold components of second jaw (444) in alignment during a welding process or other bonding process, such that the pins are removed after the welding/bonding process is complete.

Outer plates (420), intermediate plates (422), and inner plates (424) may be constructed differently to accomplish different functions. For instance, outer plates (420) may be constructed of a metal for providing strength to jaw (444). Intermediate plates (422) may be constructed to have a PTC material in a top portion and an electrode and insulator in the bottom portion Inner plates (424) could be constructed to include teeth or just include a strong material Inner plates (424) may be configured to contact firing beam (460) while neither intermediate plates (422) nor outer plates (420) contact firing beam (460). Thus, as firing beam (460) is advanced distally through end effector (440), firing beam (460) bears against inner plates (424) to drive jaw (444) pivotally toward jaw (442) about pin (472). Outer plates (420), intermediate plates (422), and inner plates (424) may also be constructed of a variety of combinations of materials. For instance, plastic, carbon fiber, titanium, stainless steel, spinoidal bronze, or any other suitable material(s) may be used as will be apparent to those of ordinary skill in the art in view of the teachings herein. In some versions, a silver coated stainless steel layer is used to draw heat from tissue.

This layer may interposed between stainless steel inner and outer layers. In addition or in the alternative, plastic outer layers may reduce heat transmission to surrounding tissue. It should also be understood that various kinds of features may be incorporated into any of the various layers of end effector (440), including but not limited to thermocouples, strain gauges, LED lights, etc. Any other number of layers may be used and layers may have any suitable thicknesses.

FIGS. 17-20 show another exemplary end effector (540) that may be readily incorporated into instrument (10) as a substitute for end effector (40). End effector (540) of this example comprises a first jaw (542) and a second jaw (544), each of which is formed by a set of layered pieces. Unlike other jaws described herein, jaws (542, 544) of this example are both configured to move bilaterally toward and away from each other with a spring pivot. End effector (540) of this example further comprises an outer sheath (532) secured to the proximal end of jaws (542, 544) and a firing beam (560) that is operable to translate through jaws (542, 544). It will be appreciated that firing beam (560) and outer sheath (532) may be substantially similar to firing beam (160) and outer sheath (132) described above. In particular, firing beam (560) with distal sharp edge (596) is operable to translate distally through end effector (540) to drive jaws (542, 544) toward each other and then sever tissue clamped between first jaw (542) and second jaw (544).

Figure 20:
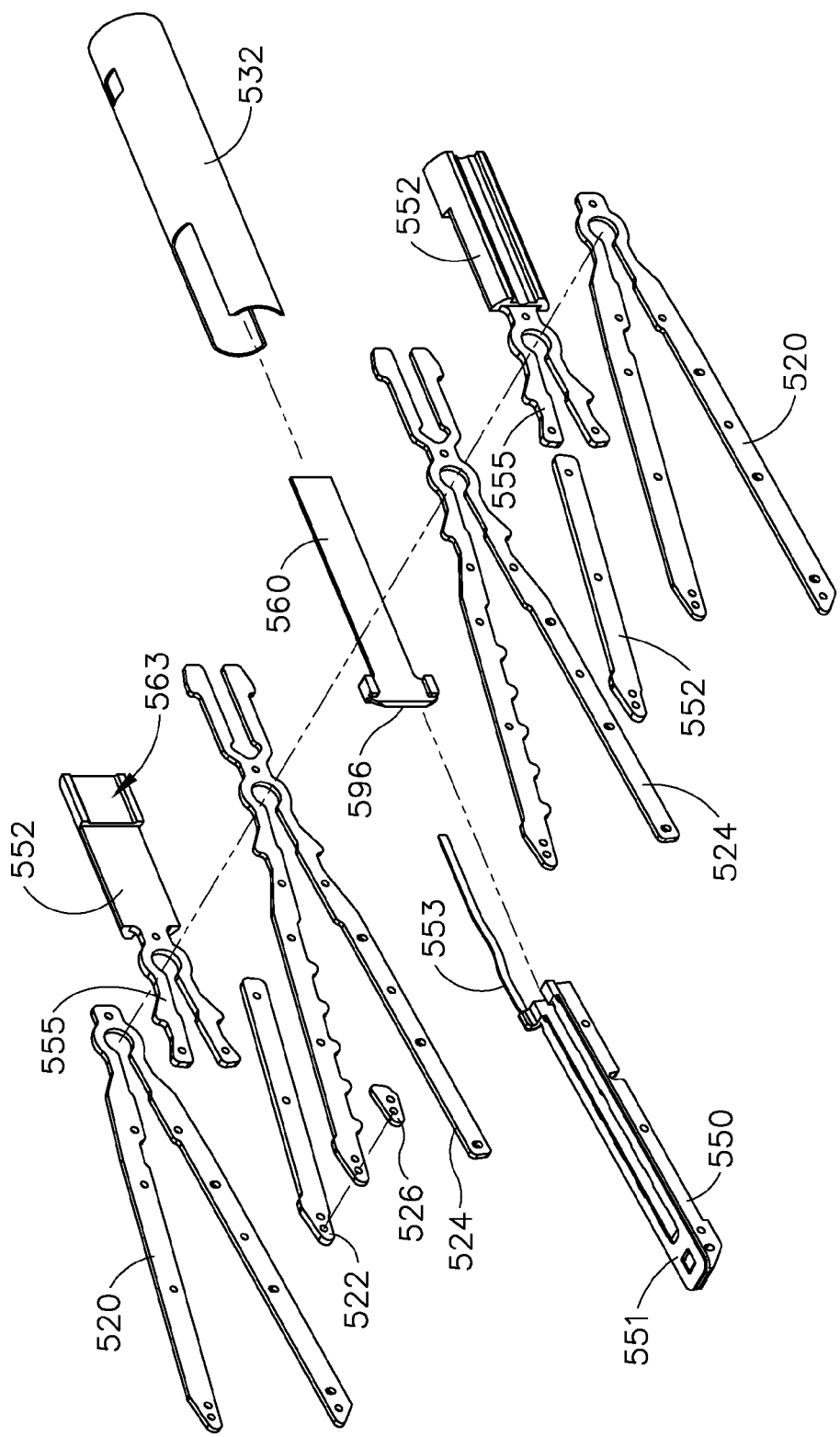
FIG. 20 depicts a perspective, exploded view of the end effector of FIG. 17.

As best seen in FIG. 20, first jaw (542) and second jaw (544) are both formed using layers comprising two outer plates (520), two inner plates (524), two intermediate plates (522), and two rear plate portions (552). Rear plate portions (552) are secured together and are further secured to outer sheath (532) to provide a frame ground. Rear plate portions (552) have recesses (563) that cooperate to form a channel that slidingly receives firing beam (560). Rear plate portions (552) also include distally projecting fork portions (555) that are interposed between respective sets of outer plates (520) and inner plates (524). Intermediate plates (522) are also interposed between respective sets of outer plates (520) and inner plates (524), such that fork portions (555) and intermediate plates (522) on each side of firing beam (560) lie along common planes. A spacer (526) is interposed between inner plates (524) and is configured to maintain a lateral spacing between inner plates (524). In particular, spacer (526) is operable to provide sufficient clearance between inner plates (524) such that firing beam (560) can advance between inner plates (524).

A lower jaw body (550) is secured to the lower prongs of inner plates (524) and outer plates (520). Lower jaw body (550) comprises a molded plastic body with an overmolded conductive electrode surface (551). Of course, electrode surface (551) may have any other suitable construction. Electrode surface (551) is in communication with an activation conduit (553) that is operable to provide electrical energy to electrode surface (551). The various layers of end effector (540) may be secured together with welding, pins through openings (528, 529), rivets through openings (528, 529), and/or any other suitable means. The various layers of end effector (540) may also be constructed of various materials. For instance, plastic, carbon fiber, titanium, stainless steel, spinoidal bronze, or any other suitable material(s) may be used as will be apparent to those of ordinary skill in the art in view of the teachings herein. In some versions, a silver coated stainless steel layer is used to draw heat from tissue. This layer may interposed between stainless steel inner and outer layers. In addition or in the alternative, plastic outer layers may reduce heat transmission to surrounding tissue. It should also be understood that various kinds of features may be incorporated into any of the various layers of end effector (540), including but not limited to thermocouples, strain gauges, LED lights, etc. Any other number of layers may be used and layers may have any suitable thicknesses.

VI. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, now U.S. Pat. No. 9,161,803, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

In versions where the teachings herein are applied to a surgical stapling instrument, it should be understood that the teachings herein may be combined with the teachings of one or more of the following, the disclosures of all of which are incorporated by reference herein: U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument,"

issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, now U.S. Pat. No. 8,408,439, issued Apr. 2, 2013; and U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued Jun. 4, 2013. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a body;
   (b) a shaft assembly extending distally from the body, wherein the shaft assembly defines a longitudinal axis; and
   (c) an end effector in communication with the shaft assembly, wherein the end effector comprises:
       (i) a first jaw comprising a hinge seat,
       (ii) a second jaw comprising:
           (A) a proximal portion,
           (B) a distal portion, and
           (C) a movable hinge configured to engage the hinge seat, wherein the second jaw is moveable relative to the first jaw between a first position, a second position, and a third position, and
       (iii) a firing beam comprising a first engagement member, wherein the firing beam is operable to translate relative to the first jaw and the second jaw,
       wherein the second jaw in the first position is open relative to the first jaw,
       wherein the second jaw in the second position is positioned such that the distal portion is closer to the first jaw than the proximal portion, wherein the first engagement member is configured to drive against a portion of the second jaw such that the moveable hinge moves from the hinge seat perpendicularly or obliquely relative to the longitudinal axis of the shaft assembly as the second jaw moves from the first position to the second position,
       wherein the second jaw in the third position is parallel to the first jaw.

2. The apparatus of claim 1, wherein the portion of the second jaw comprises a cross beam, wherein the first engagement member is configured to engage the cross beam.

3. The apparatus of claim 1, wherein the first engagement member is configured to engage the proximal portion of the second jaw to drive the proximal portion of second jaw toward the first jaw.

4. The apparatus of claim 1, wherein the firing beam further includes a second engagement member, wherein the second engagement member is operable to bear against the second jaw to drive the second jaw toward the first jaw.

5. The apparatus of claim 4, wherein the second jaw includes an undulating portion, wherein the second engagement member is configured to traverse the undulating portion.

6. The apparatus of claim 4, wherein the second engagement member is distal to the first engagement member.

7. The apparatus of claim 1, wherein the first engagement member comprises a pin.

8. The apparatus of claim 1, wherein the second jaw comprises a plurality of teeth configured to grip tissue, wherein at least one of the teeth has a rounded inner portion.

9. The apparatus of claim 1, wherein the end effector further comprises a cylindraceous electrode extending through the first jaw or the second jaw.

10. The apparatus of claim 9, wherein the cylindraceous electrode forms a rounded distal portion.

11. The apparatus of claim 1, wherein the end effector comprises an electrosurgical end effector.

12. The apparatus of claim 1, further comprising a resilient member in communication with the second jaw, wherein the resilient member is in communication with an engagement portion of the second jaw.

13. The apparatus of claim 12, wherein the resilient member comprises a bent leaf spring.

14. An apparatus for operating on tissue, the apparatus comprising:
   (a) a body;
   (b) a shaft assembly extending distally from the body; and
   (c) an end effector in communication with the shaft assembly, wherein the end effector comprises:
       (i) a first jaw comprising a first proximal portion, and a first distal portion,
       (ii) a second jaw comprising a second proximal portion, a second distal portion, and an undulating portion, wherein the second jaw is moveable relative to the first jaw between a first position, a second position, and a third position, and
       (iii) a firing beam comprising a first engagement member, wherein the firing beam is configured to translate from the first proximal portion toward the first distal portion,
       wherein the second jaw in the first position is open relative to the first jaw such that the second distal portion is further away from the first distal portion as compared to a first distance defined between the second proximal portion and the first proximal portion,
       wherein the second jaw in the second position is positioned such that the second distal portion is closer to the first distal portion as compared to a second distance defined between the second proximal portion and the first proximal portion,
       wherein the second jaw in the third position is parallel to the first jaw, wherein the first engagement member is configured to contact the undulating portion in order to move the second jaw from the second position to the third position.

15. The apparatus of claim 14, wherein translation of the firing beam from the first proximal portion to the first distal portion is operable to move second jaw to the first position, the second position, and the third position.

16. The apparatus of claim 14, wherein the second jaw is rotatable about a first axis of rotation from the first position to the second position, wherein the second jaw is rotatable about a second axis of rotation from the second position to the third position.

17. An apparatus for operating on tissue, the apparatus comprising:
(a) a body;
(b) a shaft assembly extending distally from the body; and
(c) an end effector in communication with the shaft assembly, wherein the end effector comprises:
 (i) a first jaw,
 (ii) a second jaw comprising:
  (A) a proximal portion,
  (B) a distal portion,
  (C) a first portion, and
  (D) a second portion,
 (iii) a firing beam comprising a first member and a second member, wherein the firing beam is configured to travel from the proximal portion of the second jaw to the distal portion of the second jaw,
wherein the firing beam is configured to drive the second jaw relative to the first jaw between a first position, a second position, and a third position,
wherein the second jaw in the first position is open relative to the first jaw,
wherein the second jaw in the second position is positioned such that the distal portion is closer to the first jaw than the proximal portion, wherein the first member of the firing beam is configured to contact the first portion of the second jaw to drive the second jaw to the second position,
wherein the second jaw in the third position is parallel to the first jaw, wherein the first member and the second member are configured to contact the second portion of the second jaw to drive the second jaw to the third position.

* * * * *